(12) United States Patent
Takuwa et al.

(10) Patent No.: US 10,238,787 B2
(45) Date of Patent: Mar. 26, 2019

(54) BLOOD COMPONENT SEPARATION DEVICE

(71) Applicants: JMS CO., LTD., Hiroshima-shi, Hiroshima (JP); JIMRO CO., LTD., Takasaki-shi, Gunma (JP)

(72) Inventors: Hiroaki Takuwa, Hiroshima (JP); Satoshi Hirai, Hiroshima (JP); Yoshiki Tanaka, Hiroshima (JP); Shuji Nakamura, Gunma (JP); Katsuyuki Sado, Gunma (JP); Kenta Kaneda, Gunma (JP)

(73) Assignee: TRANSELL Co., Ltd., Tokyo (JP)

( * ) Notice: Subject to any disclaimer, the term of this patent is extended or adjusted under 35 U.S.C. 154(b) by 378 days.

(21) Appl. No.: 15/024,570

(22) PCT Filed: Aug. 21, 2014

(86) PCT No.: PCT/JP2014/071854
§ 371 (c)(1),
(2) Date: Mar. 24, 2016

(87) PCT Pub. No.: WO2015/045688
PCT Pub. Date: Apr. 2, 2015

(65) Prior Publication Data
US 2016/0235906 A1  Aug. 18, 2016

(30) Foreign Application Priority Data

Sep. 25, 2013 (JP) ................................. 2013-198558

(51) Int. Cl.
*A61M 1/36* (2006.01)
*A61J 1/14* (2006.01)
(Continued)

(52) U.S. Cl.
CPC .......... *A61M 1/3693* (2013.01); *A61J 1/1418* (2015.05); *A61J 1/1475* (2013.01);
(Continued)

(58) Field of Classification Search
CPC ........ A61J 1/067; A61J 1/1418; A61J 1/1475; A61J 1/2003; A61M 1/029; A61M 1/3693; A61M 2202/0415; A61M 2202/0429
See application file for complete search history.

(56) References Cited

U.S. PATENT DOCUMENTS 5,632,906 A * 5/1997 Ishida .................. A61M 1/029
210/109

FOREIGN PATENT DOCUMENTS

CN     201816872 U     5/2011
JP     1-501528        6/1989
(Continued)

OTHER PUBLICATIONS

International Search Report issued in International Application No. PCT/JP2014/071854, dated Nov. 18, 2014, 4 pages.
(Continued)

*Primary Examiner* — Benjamin Klein
(74) *Attorney, Agent, or Firm* — Hamre, Schumann, Mueller & Larson, P.C.

(57) ABSTRACT

A blood reservoir (20) for storing blood includes a first storage section (21), a second storage section (22), and a third storage section (23) that is provided between the first storage section and the second storage section, and communicates with the first storage section and the second storage section. A volume of the blood reservoir (20) can be adjusted by changing the amount of expansion or contraction of a bellows structure (28) using a bellows adjustment mechanism (83, 93).

22 Claims, 26 Drawing Sheets

(51) Int. Cl.
- *A61J 1/20* (2006.01)
- *A61M 1/02* (2006.01)
- *A61J 1/22* (2006.01)
- *A61J 1/06* (2006.01)

(52) U.S. Cl.
CPC ............... *A61J 1/2003* (2015.05); *A61J 1/22* (2013.01); *A61M 1/029* (2013.01); *A61J 1/067* (2013.01); *A61M 2202/0415* (2013.01); *A61M 2202/0429* (2013.01)

(56) References Cited

FOREIGN PATENT DOCUMENTS

| | | |
|---|---|---|
| JP | 6-014992 | 1/1994 |
| JP | 9-206356 | 8/1997 |
| JP | 2002-291874 | 10/2002 |
| JP | 4431929 B | 3/2010 |
| JP | 2011-055916 | 3/2011 |
| JP | 2014-079442 | 5/2014 |
| WO | 88/04559 | 6/1988 |
| WO | 2013/015419 | 1/2013 |
| WO | 2013/146505 | 10/2013 |

OTHER PUBLICATIONS

Office Action issued in corresponding Chinese Patent Application No. 201480053104.7, dated May 24, 2018, 7 pages.

* cited by examiner

BLOOD COMPONENT SEPARATION DEVICE

TECHNICAL FIELD

The present invention relates to a blood component separation device used for separating blood into different blood components by centrifugation.

BACKGROUND ART

In recent years, whole blood transfusion is being replaced by blood component transfusion in which only necessary components in blood are transfused into a patient, and further plasma sampling for producing a plasma preparation is being performed. Therefore, the separation of blood into blood components is carried out in the field of blood industry. In this case, blood, which is conventionally contained in a plastic blood bag, is centrifuged and separated into different components such as red blood cells, white blood cells, and platelets by using their differences in specific gravity, so that necessary components are extracted.

As illustrated in FIG. 25, a conventional blood bag 800 used for the separation of blood into blood components includes a substantially rectangular plastic bag body 801, a port 802, and transfer tubes 811, 812, 813. The port 802 and the transfer tubes 811, 812, 813 communicate with the bag body 801. The ends of the transfer tubes 812, 813 are connected to sub-bags (not illustrated) for storing separated blood components (plasma components and white blood cell components), respectively.

The separation of blood into blood components with the use of the blood bag 800 is performed in the following manner. First, the collected blood is stored in the bag body 801 via the transfer tube 811. At this time, the port 802 and the transfer tubes 812, 813 are closed. Next, the blood in the bag body 801 is centrifuged and separated into a red blood cell layer A, a plasma layer B, and a white blood cell layer C containing platelets, as illustrated in FIG. 25. Subsequently, the transfer tube 812 is opened, and pressure is applied to the bag body 801 so that the plasma layer B is transferred via the transfer tube 812 and into a sub-bag (not illustrated) that is connected to the end of this transfer tube 812. Then, the transfer tube 813 is opened, and pressure is applied to the bag body 801 so that the white blood cell layer C is transferred via the transfer tube 813 and into another sub-bag (not illustrated) that is connected to the end of this transfer tube 813. Thus, the separation of the collected blood into each of the blood components is completed.

The proportion of white blood cell components is lower than that of the other components in blood. Therefore, in the conventional blood bag 800 as illustrated in FIG. 25, the white blood cell layer C is separated as a very thin layer between the red blood cell layer A and the plasma layer B. It is not easy for the above method to transfer all the white blood cell components to the sub-bag via the transfer tube 813 without mixing the red blood cell components into the white blood cell components or without leaving the white blood cell components in the red blood cell layer A. When the white blood cell layer C is transferred to the sub-bag by moving it in the bag body 801, the white blood cell components adhere to the inner surface of the bag body 801. This makes it difficult to collect all the white blood cell components.

A blood bag that is used for the separation of blood into blood components and can solve the above problems has been proposed (see, e.g., Patent Document 1). This blood bag will be described with reference to FIG. 26.

As illustrated in FIG. 26, the blood bag 900 used for the separation of blood into blood components includes a bag body 901 for storing blood and a transfer tube 902 for transferring the collected blood to the bag body 901. The bag body 901 includes a first bag portion 911 and a second bag portion 912 on both ends, and a third bag portion 913 provided between the first bag portion 911 and the second bag portion 912. The third bag portion 913 is narrower in width than the first bag portion 911 and the second bag portion 912. The first bag portion 911, the second bag portion 912, and the third bag portion 913 have a first port 921, a second port 922, and a third port 923, from which the contents are taken, respectively.

The separation of blood into blood components with the use of the blood bag 900 is performed in the following manner. First, blood is stored in the bag body 901 via the transfer tube 902. Next, blood in the bag body 901 is centrifuged. The blood is separated into a red blood cell layer A in the first bag portion 911, a plasma layer B in the second bag portion 912, and a white blood cell layer C in the third bag portion 913. Subsequently, both the boundary portion between the first bag portion 911 and the third bag portion 913, and the boundary portion between the third bag portion 913 and the second bag portion 912 are sealed. The sealing may be performed by, e.g., a heat sealing method or a high-frequency sealing method. Then, the bag body 901 is cut into the first, second, and third bag portions 911, 912, 913 along the sealed portions. The red blood cell layer A in the first bag portion 911, the plasma layer B in the second bag portion 912, and the white blood cell layer C in the third bag portion 913 are taken out via the first port 921, the second port 922, and the third port 923, respectively.

As described above, the blood bag 900 is configured so that the bag body 901 can be sealed for each component and separated after centrifugation. Therefore, the blood can be separated into different pure blood components without any mixing of other blood components. In particular, the rate of collection of white blood cell components can be improved.

PRIOR ART DOCUMENTS

Patent Documents

Patent Document 1: Japanese Patent No. 4431929

DISCLOSURE OF INVENTION

Problem to be Solved by the Invention

A red blood cell volume and a plasma volume differ depending on the hematocrit value and the blood volume of blood. The hematocrit value shows the ratio of the volume of blood cells to the total volume of blood. The normal value is about 40 to 50% for adult men and about 35 to 45% for adult women. The hematocrit value may be either lower or higher than the normal value for any reason. If the hematocrit value and the blood volume vary, the position of the white blood cell layer that is to be formed in the blood bag after centrifugation will be changed.

Therefore, when blood is stored in the conventional blood bag 900 (see FIG. 26) and centrifuged, the white blood cell layer C is not always formed within the third bag portion 913. If the white blood cell layer C is deviated from the third bag portion 913, the first bag portion 911 or the second bag portion 912 can be squeezed to move the white blood cell layer C back to the third bag portion 913. However, such an operation allows different components to be mixed with each other, and thus the rate of collection of white blood cell components is reduced.

The first object of the present invention is to provide a blood component separation device that allows a white blood cell layer (also called a "buffy coat") to be stably formed in a desired position after centrifugation. The second object of the present invention is to provide a blood component separation device that improves the rate of collection of white blood cell components.

Means for Solving Problem

A blood component separation device of the present invention includes a blood reservoir for storing blood and is used for centrifugation of blood stored in the blood reservoir. The blood reservoir includes a first storage section, a second storage section, and a third storage section that is provided between the first storage section and the second storage section, and communicates with the first storage section and the second storage section. The blood component separation device further includes a bellows structure provided on the blood reservoir and a bellows adjustment mechanism for adjusting an amount of expansion or contraction of the bellows structure. A volume of the blood reservoir can be adjusted by changing the amount of expansion or contraction of the bellows structure using the bellows adjustment mechanism.

Effects of the Invention

The present invention can adjust the volume of the blood reservoir by adjusting the amount of expansion or contraction of the bellows structure in accordance with the blood volume and the hematocrit value of blood to be centrifuged. Thus, the position of the buffy coat after centrifugation can always be aligned with the third storage section regardless of the blood volume and the hematocrit value of blood to be centrifuged. Consequently, the rate of collection of white blood cell components can be improved. The bellows structure has a simple configuration, and therefore is advantageous in reliability, durability, and cost reduction.

DESCRIPTION OF THE INVENTION

Figure 1:
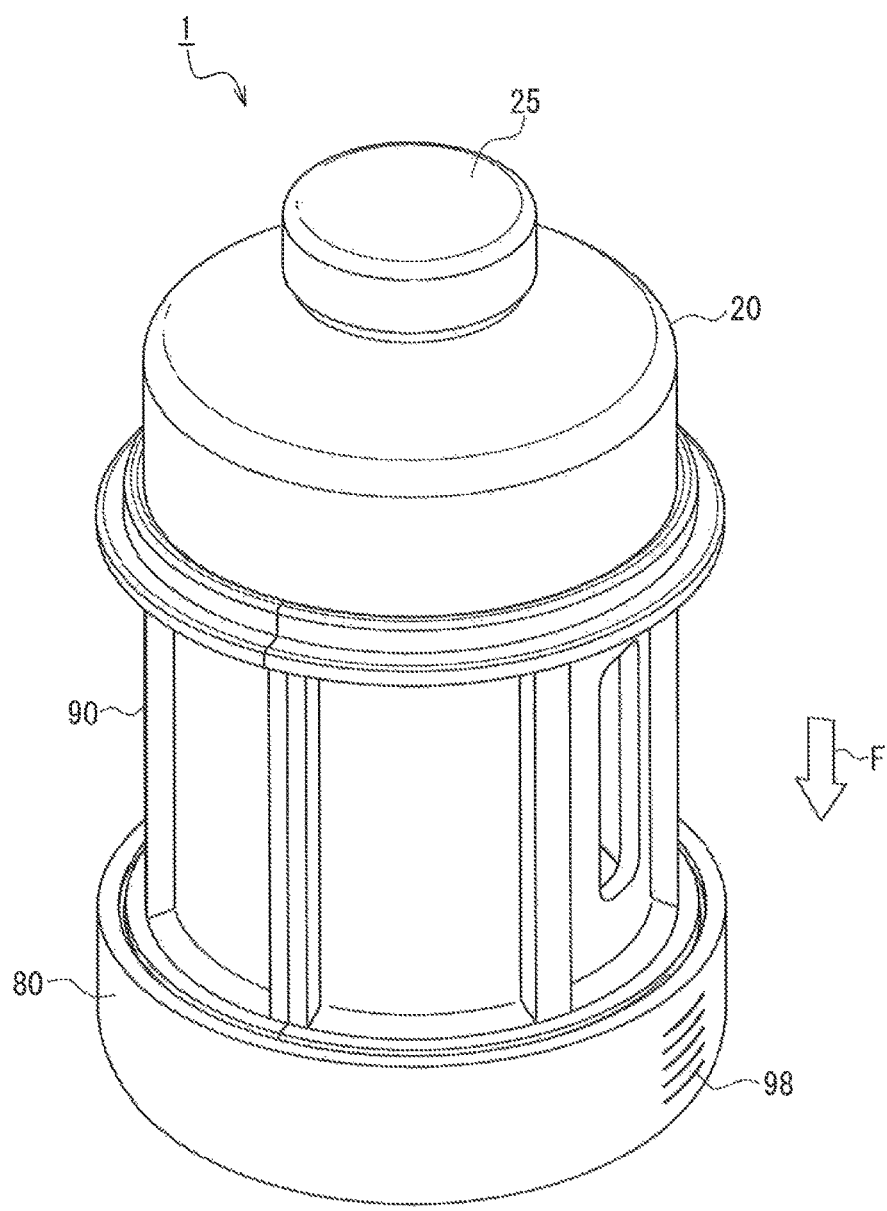
FIG. 1 is a perspective view of a blood component separation device of Embodiment 1 of the present invention.

In the blood component separation device of the present invention, it is preferable that the bellows structure is provided on the first storage section that stores red blood cell components after centrifugation. Thus, the position of the buffy coat after centrifugation can be easily aligned with the third storage section.

It is preferable that the blood reservoir is integrally formed as a single piece, including the bellows structure. This can reduce the possibility that the blood that is subjected to pressure exerted by the centrifugal force during centrifugation will leak out of the blood reservoir. Moreover, this can facilitate the manufacture of the blood reservoir and thus reduce the cost.

The bellows adjustment mechanism may include a male thread and a female thread. In this case, it is preferable that the amount of expansion or contraction of the bellows structure can be adjusted by adjusting the depth of screwing of the male thread into the female thread. Thus, the bellows adjustment mechanism has a simple configuration, and therefore is advantageous in reliability, durability, and cost reduction. Moreover, it is easy to make the fine adjustment of the amount of contraction of the bellows structure, and further to make the fine adjustment of the volume of the blood reservoir.

The blood component separation device of the present invention may further include a support member that prevents deformation of the third storage section during centrifugation, and a bottom cap that is in contact with at least a part of a bottom of the first storage section. In this case, it is preferable that one of the support member and the bottom cap has the male thread, and the other has the female thread. Thus, the bellows adjustment mechanism can be configured while suppressing an increase in the number of parts and an increase in complexity of the structure.

The bottom cap or the support member may have a scale that serves as an indicator for adjusting the amount of expansion or contraction of the bellows structure. Thus, the operation of adjusting the volume of the blood reservoir in accordance with blood can be easily and quickly performed.

It is preferable that the blood component separation device of the present invention is configured so that a communication between the first storage section and the third storage section can be blocked, and a communication between the second storage section and the third storage section can be blocked. Thus, white blood cell components can be efficiently collected after centrifugation without any mixing of other components.

The blood component separation device of the present invention may further include a flow path through which blood components in the third storage section flow out of the blood reservoir. Thus, white blood cell components can be efficiently collected after centrifugation.

The blood component separation device of the present invention may include a first blocking member and a second blocking member in the blood reservoir. In this case, it is preferable that the first blocking member is configured to be able to block the communication between the first storage section and the third storage section. It is preferable that the second blocking member is configured to be able to block the communication between the second storage section and the third storage section. Unlike the conventional blood bag, this preferred aspect can block the communication between the adjacent storage sections without the need to deform or squeeze the blood reservoir in the boundary portion between the adjacent storage sections. This aspect can reduce the possibility that the blood components stored in the respective adjacent storage sections will be mixed together when the communication between the adjacent storage sections is blocked after centrifugation. Therefore, this is advantageous to improve the collection efficiency of white blood cell components. Moreover, the third storage section can have a relatively large inner diameter. This is advantageous to further improve the collection efficiency of white blood cell components.

It is preferable that the first blocking member moves in the first storage section to block the communication between the first storage section and the third storage section. Moreover, it is preferable that the second blocking member moves in the second storage section to block the communication between the second storage section and the third storage section. This preferred aspect eliminates the need to substantially deform the first blocking member and the second blocking member themselves in order to block the communication. Therefore, this aspect improves the liquid tightness when the communication between the adjacent storage sections is blocked. This is advantageous to efficiently collect white blood cell components.

It is preferable that the blood component separation device includes a first rod that holds the first blocking member and is drawn out of the blood reservoir. In this case, it is preferable that the first rod is moved to allow the first blocking member to move. In this preferred aspect, the first blocking member can be easily moved from the outside of the blood reservoir and block the communication between the first storage section and the third storage section.

It is preferable that the blood component separation device includes a first flow path that provides a communication between the third storage section and the outside of the blood reservoir while the first blocking member blocks the communication between the first storage section and the third storage section, and the second blocking member blocks the communication between the second storage section and the third storage section. In this preferred aspect, white blood cell components in the third storage section can be collected via the first flow path.

It is preferable that the blood component separation device further includes a second flow path that provides a communication between the third storage section and the outside of the blood reservoir while the first blocking member blocks the communication between the first storage section and the third storage section, and the second blocking member blocks the communication between the second storage section and the third storage section. In this preferred aspect, white blood cell components in the third storage section can be smoothly collected while variations in the pressure in the third storage section are suppressed.

It is preferable that at least one of the first flow path and the second flow path is provided in the first rod. In this preferred aspect, the number of parts of the device can be reduced, and thus the configuration of the device can be simplified, compared to the case where the first flow path and the second flow path are formed outside the first rod.

The first rod may have a double tube structure in which the inner tube is inserted into the outer tube. In this case, it is preferable that the first flow path is formed in the inner tube, and the second flow path is formed between the inner tube and the outer tube. In this preferred aspect, the mutually independent first flow path and second flow path can be provided in the same first rod with a simple configuration.

It is preferable that the first blocking member can be placed in contact with the bottom surface of the first storage section. In this preferred aspect, the first blocking member can be stably held during centrifugation.

It is preferable that the blood component separation device includes a second rod that holds the second blocking member and is drawn out of the blood reservoir. In this case, it is preferable that the second rod is moved to allow the second blocking member to move. In this preferred aspect, the second blocking member can be easily moved from the outside of the blood reservoir and block the communication between the second storage section and the third storage section.

It is preferable that the blood component separation device further includes a movement restriction mechanism that restricts a movement of the second blocking member so as to prevent the second blocking member from moving in the blood reservoir and blocking the communication between the second storage section and the third storage section during centrifugation. In this preferred aspect, the second blocking member can be stably held during centrifugation.

It is preferable that the movement restriction mechanism includes a removable stopper that is provided outside the blood reservoir. In this preferred aspect, the stopper is removed after centrifugation, and then the second blocking member can be moved. Therefore, the second blocking member can be simply configured so that the movement of the second blocking member is restricted during centrifugation, but is allowed after centrifugation.

Alternatively, the movement restriction mechanism may include a stopper that is provided outside the blood reservoir and coupled to the second rod. This preferred configuration can prevent the stopper from being lost. Even if the length of the second rod is reduced, the second blocking member can be moved by operating the stopper.

It is preferable that the blood component separation device of the present invention further includes a pressure release mechanism that releases pressure in the third storage section when the first blocking member blocks the communication between the first storage section and the third storage section, and the second blocking member blocks the communication between the second storage section and the third storage section. This preferred configuration can reduce the possibility that an increase in the pressure in the third storage section will cause the white blood cell components in the third storage section to leak to the outside through the first flow path or the second flow path, or will make it difficult to block the communication between the third storage section and the second storage section by the second blocking member.

It is preferable that the pressure release mechanism includes a through hole formed in the second blocking member so as to provide a communication between the second storage section and the third storage section. With this preferred configuration, the pressure release mechanism can have a simple configuration.

The pressure release mechanism may further include a one-way valve provided in the through hole. In this case, it is preferable that the one-way valve allows a flow from the third storage section to the second storage section through the through hole, and prevents a flow from the second storage section to the third storage section through the through hole. With this preferred configuration, the pressure release mechanism can have a simple configuration.

Alternatively, the pressure release mechanism may further include a tube, one end of which is connected to the through hole. In this case, it is preferable that the other end of the tube is open in a position above a blood surface in the blood reservoir. This preferred configuration can provide the pressure release mechanism with improved operational reliability.

It is preferable that the pressure release mechanism forms a flow path for introducing outside air into the third storage section when white blood cell components in the third storage section are aspirated and collected while the first blocking member blocks the communication between the first storage section and the third storage section, and the second blocking member blocks the communication between the second storage section and the third storage section. In this preferred configuration, white blood cell components in the third storage section can be smoothly collected while variations in the pressure in the third storage section are suppressed. Moreover, there is no need to form the flow path for introducing outside air into the third storage section in addition to the pressure release mechanism. Therefore, the number of parts of the blood component separation device can be reduced, and thus the configuration of the device can be simplified.

Hereinafter, the present invention will be described in detail with reference to preferred embodiments. Needless to say, the present invention is not limited to the following embodiments. For convenience, each of the drawings referred to in the following description schematically illustrates only the main members of constituent members in the embodiments that are required for the explanation of the present invention. Therefore, the present invention may include any members that are not illustrated in the following drawings. Each of the following drawings does not exactly represent the size, the size ratio, etc. of the actual members.

(Embodiment 1)

Embodiment 1 describes a basic configuration of a blood component separation device that includes a volume adjustment mechanism for adjusting the volume of a blood reservoir.

[Configuration of Blood Component Separation Device]

Figure 2:
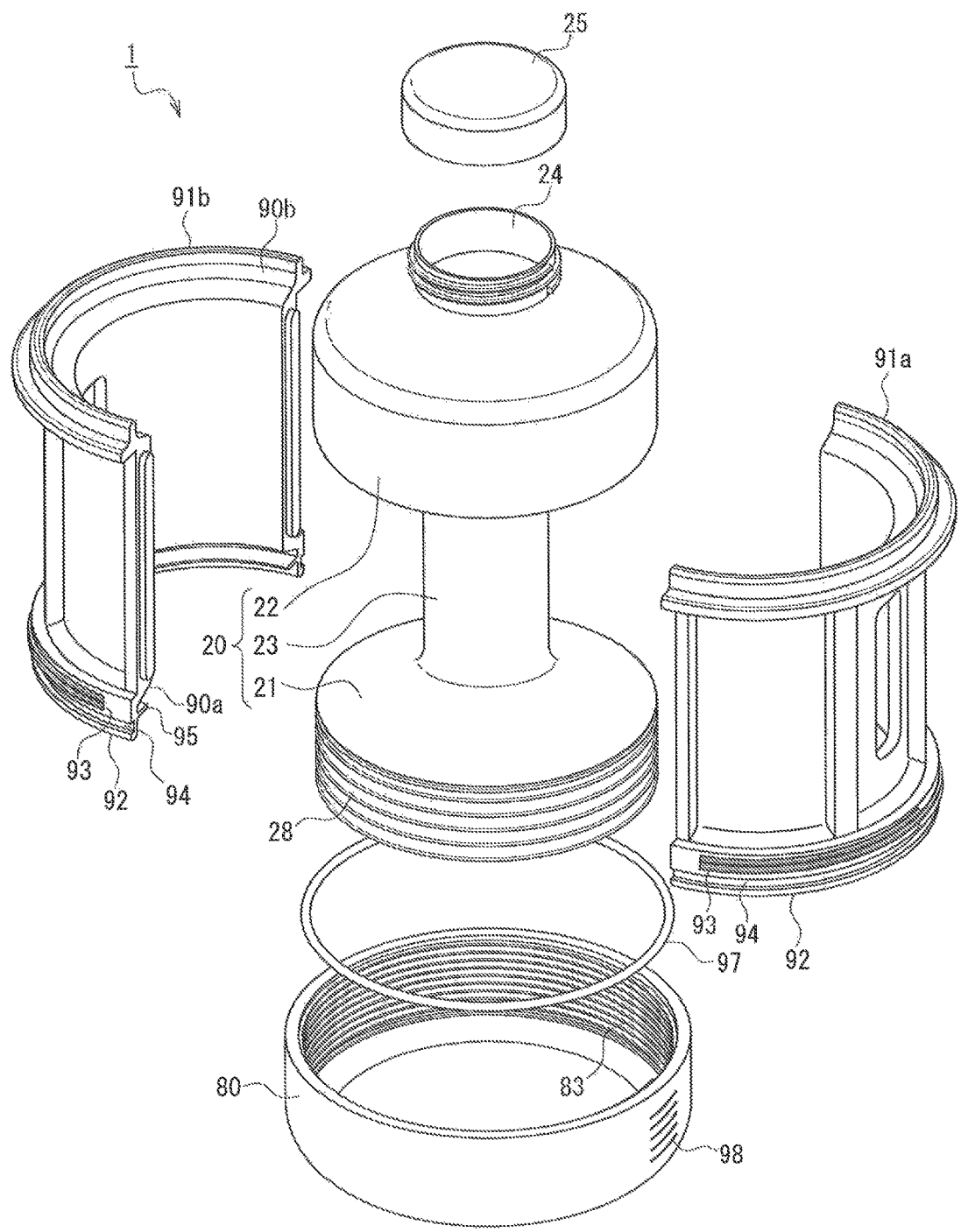
FIG. 2 is an exploded perspective view of a blood component separation device of Embodiment 1 of the present invention.
Figure 3:
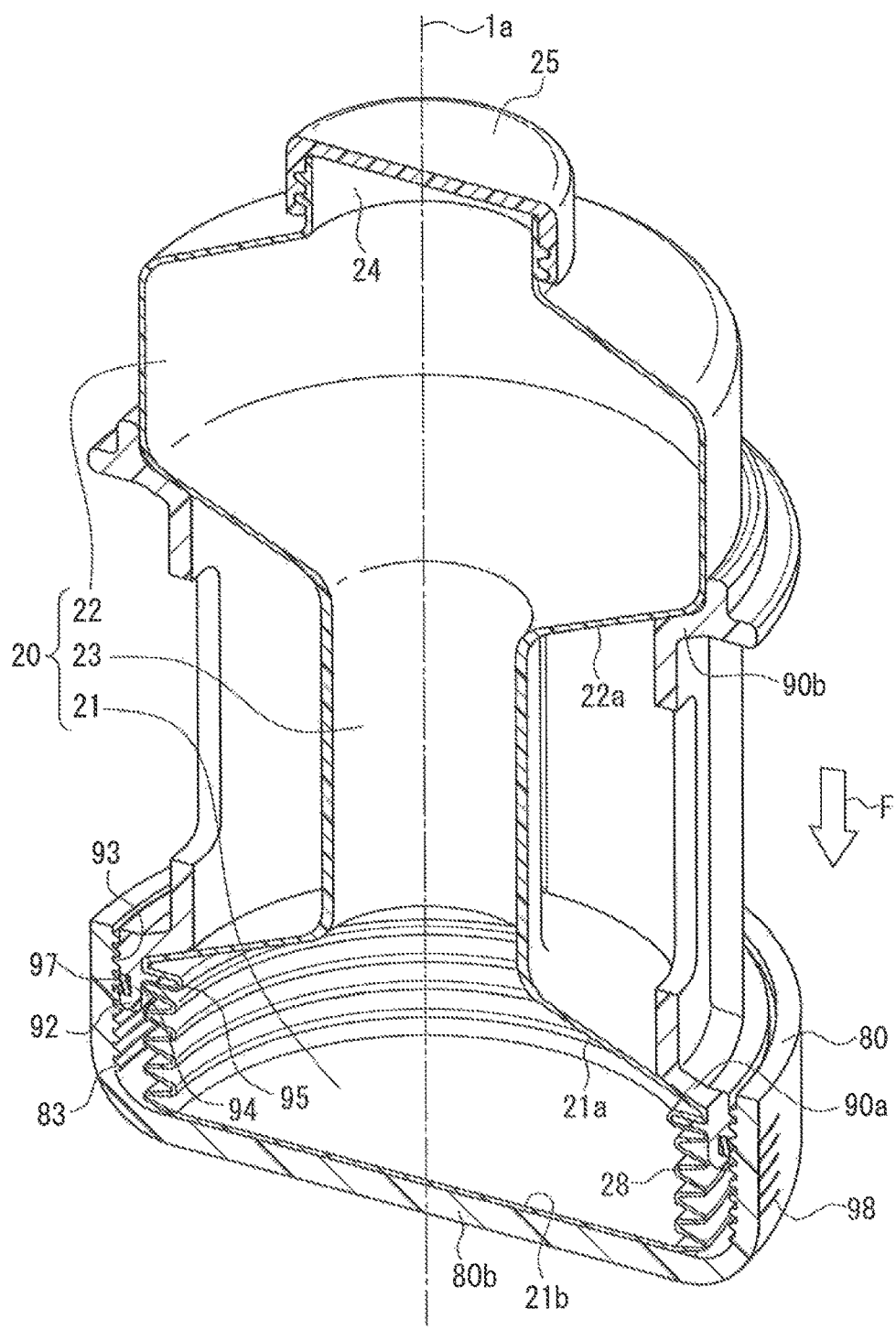
FIG. 3 is a cross-sectional perspective view of a blood component separation device of Embodiment 1 of the present invention.

FIG. 1 is a schematic perspective view of a blood component separation device 1 (simply referred to as a "device 1" in the following) of Embodiment 1 of the present invention. FIG. 2 is an exploded perspective view of the device 1. FIG. 3 is a cross-sectional perspective view taken along the longitudinal direction of the device 1. In FIG. 3, an alternate long and short dash line 1a is a central axis of the device 1. For convenience of the following description, a direction parallel to the central axis 1a is called a "vertical direction" and a direction parallel to a plane that is perpendicular to the central axis 1a is called a "horizontal direction".

As illustrated in FIGS. 1, 2, and 3, the device 1 includes a blood reservoir 20 for storing blood. The device 1 is used to separate the blood stored in the blood reservoir 20 into different blood components by centrifugation.

As illustrated in FIG. 3, the blood reservoir 20 includes a first storage section 21, a second storage section 22, and a third storage section 23 provided between the first storage section 21 and the second storage section 22. The third storage section 23 communicates with both the first storage section 21 and the second storage section 22. Therefore, the first storage section 21 and the second storage section 22 communicate with each other via the third storage section 23. During centrifugation, the blood components can freely move from the first storage section 21 to the second storage section 22 through the third storage section 23, and vice versa. The device 1 is usually used with the first storage section 21 facing downward while the central axis 1a is pointing straight up.

Blood is injected into the blood reservoir 20 via a substantially cylindrical mouth 24 that protrudes from the center of the upper surface of the first storage section 21. When the blood is stored in the blood reservoir 20, the device 1 is mounted in a centrifuge so that the centrifugal force acts in the direction of the arrow F in FIGS. 1 and 3. After centrifugation, the first storage section 21 stores red blood cell components, the second storage section 22 stores plasma components, and the third storage section 23 stores a buffy coat containing white blood cell components and platelets. The first, second, and third storage sections 21, 22, 23 and the mouth 24 are coaxially arranged.

The first storage section 21 is hollow and substantially cylindrical in shape as a whole. The first storage section 21 has a bellows structure 28 on the outer circumferential surface. The bellows structure 28 is able to expand and/or contract in the vertical direction. The bellows structure 28 is formed such that the outer wall of the first storage section 21 is periodically folded in a zigzag manner. The expansion and contraction of the bellows structure 28 in the vertical direction can vary not only the volume of the first storage section 21, but also the volume of the blood reservoir 20.

The second storage section 22 is hollow and substantially cylindrical in shape. The outer diameter of the second storage section 22 is substantially the same as that of the first storage section 21.

The third storage section 23 is also hollow and substantially cylindrical in shape. The inner circumferential surface of the third storage section 23 is a smooth cylindrical surface with an inner diameter that is substantially constant in the direction of the central axis 1a. Since the third storage section 23, which provides a communication between the first storage section 21 and the second storage section 22, has the above inner circumferential surface, the blood components moving in the third storage section 23 during centrifugation are not likely to be retained in the third storage section 23. This means that the components of blood cells having a relatively large specific gravity (e.g., red blood cells) easily move from the second storage section 22 to the first storage section 21 through the third storage section 23, and the components having a relatively small specific gravity (e.g., plasma) easily move from the first storage section 21 to the second storage section 22 through the third storage section 23 during centrifugation. Therefore, the use of the cylindrical surface with a constant inner diameter as the inner circumferential surface of the third storage section 23 is advantageous to improve the rate of collection of white blood cell components.

The inner diameter of the third storage section 23 is smaller than that of each of the first storage section 21 and the second storage section 22. The proportion of white blood cell components in blood is relatively low. Therefore, when the inner diameter of the third storage section 23 is reduced, the thickness (i.e., the size in the vertical direction) of the buffy coat after centrifugation can be relatively large. This is advantageous to efficiently collect the white blood cell components.

The second storage section 22 has a lower wall 22a (i.e., the wall facing the third storage section 23) whose inner surface is preferably in the form of a funnel (i.e., a circular conical surface or a tapered surface) so that the inner surface is inclined downward (toward the third storage section 23) as it is closer to the central axis 1a. The inclined inner surface of the lower wall 22a makes it easy for the components of blood cells having a relatively large specific gravity (e.g., red blood cells) in the second storage section 22 to move to the first storage section 21 through the third storage section 23 during centrifugation.

Similarly, the first storage section 21 has an upper wall 21a (i.e., the wall facing the third storage section 23) whose inner surface is preferably in the form of a funnel (i.e., a circular conical surface or a tapered surface) so that the inner surface is inclined upward (toward the third storage section 23) as it is closer to the central axis 1a. The inclined inner surface of the upper wall 21a makes it easy for the components having a relatively small specific gravity (e.g., blood plasma) in the first storage section 21 to move to the second storage section 22 through the third storage section 23 during centrifugation.

In the cross section along the plane containing the central axis 1a, the inclination angle of the inner surface of the lower wall 22a of the second storage section 22 with respect to the plane along the horizontal direction, and the inclination angle of the inner surface of the upper wall 21a of the first storage section 21 with respect to the plane along the horizontal direction are not particularly limited and are preferably 10 to 45 degrees, more preferably 15 to 30 degrees, and may be set to, e.g., 20 degrees. If the inclination angles are larger than this numerical range, the volumes of the first and second storage sections 21, 22 will be reduced. If the inclination angles are smaller than this numerical range, red blood cells or white blood cells will remain in the second storage section 22, or white blood cells or plasma components will remain in the first storage section 21 after centrifugation. This leads to a reduction in the rate of collection of white blood cell components. The inner surface of the lower wall 22a of the second storage section 22 and the inner surface of the upper wall 21a of the first storage section 21 are not necessarily accurate circular conical surfaces, and may be inclined so that, e.g., the inclination angle of the inner surface of the lower wall 22a and the inclination angle of the inner surface of the upper wall 21a change with the distance from the central axis 1a in the horizontal direction.

It is preferable that the materials for the blood reservoir 20 including the first, second, and third storage sections 21, 22, 23 have a mechanical strength high enough to ensure that the shape of the blood reservoir 20 will not be changed when blood is stored in the blood reservoir 20 (i.e., the materials have shape retention properties). It is more preferable that the materials for the blood reservoir 20 have a relatively high rigidity so as to minimize the deformation caused by the centrifugal force that acts on blood during centrifugation. Further, it is preferable that the materials for the blood reservoir 20 have transparency so that the blood stored in the blood reservoir 20 can be visually observed from the outside. However, it is preferable that the bellows structure 28 is flexible to the extent that it is able to expand and contract. In view of the above, examples of the materials for the blood reservoir 20 include (but are not limited to) resin materials such as LDPE (low-density polyethylene), PP (polypropylene), and EVA (ethylene-vinyl acetate copolymer resin).

A method for manufacturing the blood reservoir 20 is not particularly limited. In this embodiment, all parts of the blood reservoir 20, including the bellows structure 28, are integrally molded in a single piece by, e.g., blow molding using the resin materials. Compared to the method of joining a plurality of parts that have been produced separately, since the blood reservoir 20 is integrally molded in a seamless manner, the method of this embodiment can reduce the possibility that the blood that is subjected to pressure exerted by the centrifugal force during centrifugation will leak out of the blood reservoir 20. Moreover, this method can facilitate the manufacture of the blood reservoir 20 and thus reduce the cost.

Of course, the blood reservoir 20 can also be manufactured by producing a plurality of members separately, and joining the members together in a liquid-tight manner. If necessary, an O ring may be provided in a joint between the adjacent members. In this case, the bellows structure 28 is preferably made of relatively soft materials, as described above. The members other than the bellows structure 28 may be made of relatively hard materials, e.g., resin materials such as polycarbonate, polyethylene, polyester, polymethylpentene, methacryl, ABS resin (acrylonitrile-butadiene-styrene copolymer), PET resin (polyethylene terephthalate), and PVC (polyvinyl chloride).

As illustrated in FIGS. 1 to 3, the mouth 24 is liquid-tightly sealed by a top cap 25. The mouth 24 has a male thread on the outer circumferential surface, and the male thread is screwed into a female thread of the top cap 25, so that the top cap 25 is fitted on the mouth 24. The top cap 25 prevents leakage of blood to the outside, e.g., when the blood reservoir 20 containing blood accidentally falls over or is subjected to an impact. The top cap 25 fitted on the mouth 24 can also serve as a handle that allows the device 1 to be held and carried around with one hand.

A support member 90 (see FIG. 1) is attached to the blood reservoir 20. In Embodiment 1, as illustrated in FIG. 2, the support member 90 is composed of two support halves 91a, 91b, and each half has a semi-cylindrical shape. The support halves 91a, 91b are attached to the blood reservoir 20 with each of them facing the third storage section 23 between the first storage section 21 and the second storage section 22. The support half 91a and the support half 91b may be joined to each other with fasteners such as screws (not shown) or by a bonding or fusion method.

As illustrated in FIG. 3, the support member 90 includes a first support portion 90a and a second support portion 90b. The first support portion 90a is in contact with and supports the upper wall 21a of the first storage section 21. The second support portion 90b is in contact with and supports the lower wall 22a of the second storage section 22. The support member 90 further includes a skirt portion 92 that extends downward from the first support portion 90a. The skirt portion 92 has a cylindrical shape and surrounds the bellows structure 28 of the first storage section 21. A male thread 93 and a groove 94 are formed on the outer circumferential surface of the skirt portion 92. The groove 94 is located adjacent to and under the male thread 93. The groove 94 is an annular groove that is continuous in the circumferential direction. An O ring 97 is fitted into the groove 94. An annular rib 95 is continuous in the circumferential direction, and protrudes from the inner circumferential surface of the skirt portion 92 toward the central axis 1a. The rib 95 is fitted into the uppermost recess of projections and recesses on the outer circumferential surface of the bellows structure 28.

The support member 90 is attached to the blood reservoir 20, and then the O ring 97 is fitted into the groove 94 of the support member 90. Subsequently, a bottom cap 80 is attached to the blood reservoir 20 from the underside. As illustrated in FIG. 2, the bottom cap 80 has a cylindrical shape with a bottom. A female thread 83 is formed on the inner circumferential surface of the cylindrical portion of the bottom cap 80. The male thread 93 of the support member 90 is screwed into the female thread 83.

Figure 4:
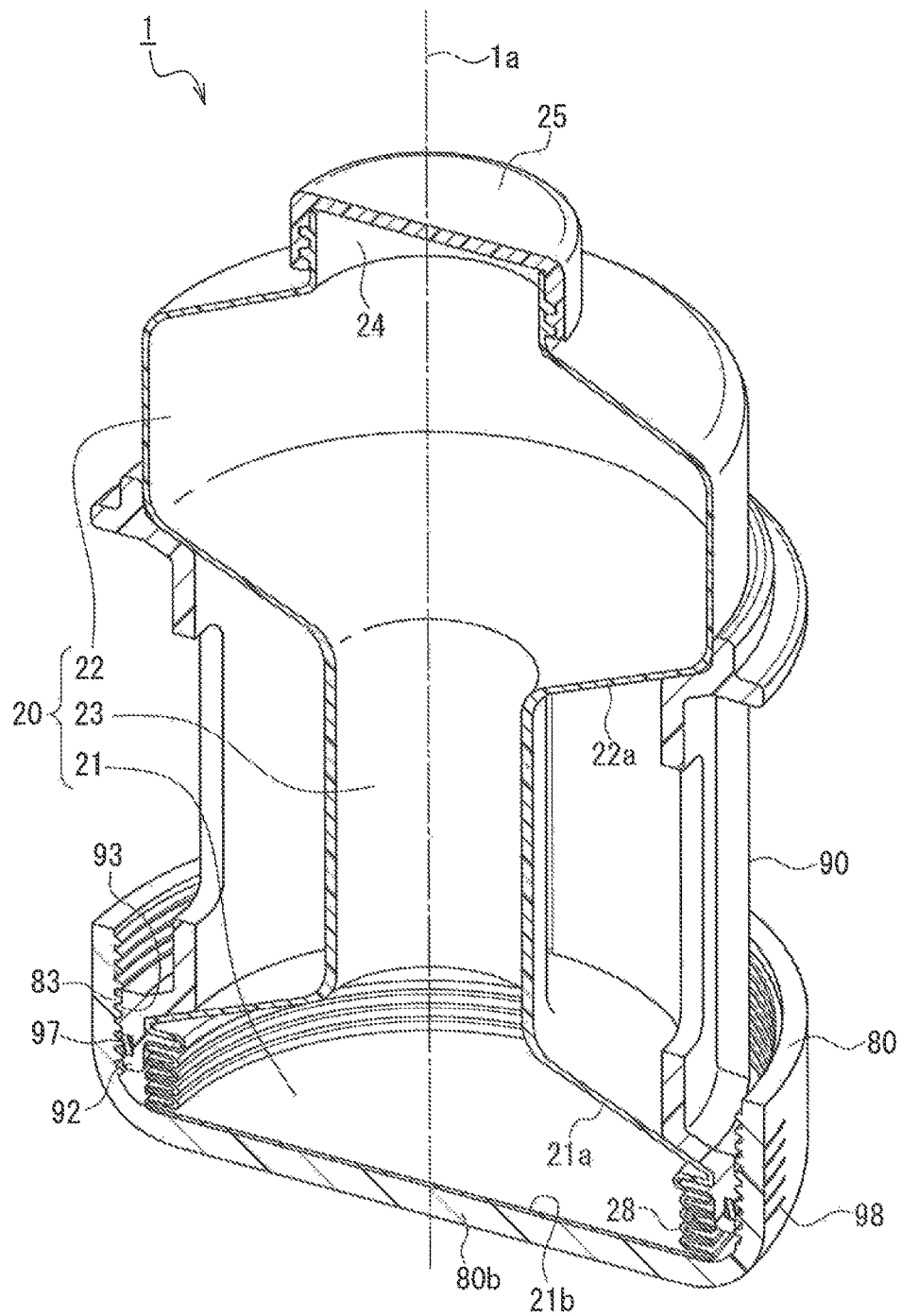
FIG. 4 is a cross-sectional perspective view of a blood component separation device of Embodiment 1 of the present invention, in which the contraction of a bellows structure is larger than that as illustrated in FIG. 3.

As described above, the first support portion 90a of the support member 90 is in contact with the upper wall 21a of the first storage section 21. Moreover, the rib 95 of the skirt portion 92 of the support member 90 is fitted into the uppermost recess of the bellows structure 28. Thus, the upper wall 21a of the first storage section 21 is held by the support member 90 in the vertical direction. A bottom 80b of the bottom cap 80 covers and is in contact with a bottom 21b of the first storage section 21. Therefore, the bellows structure 28 of the first storage section 21 contracts and deforms in the vertical direction between the support member 90 and the bottom cap 80 as the male thread 93 is screwed into the female thread 83 by rotating the bottom cap 80 relative to the support member 90. FIG. 4 is a cross-sectional perspective view of the device 1 in which the contraction deformation of the bellows structure 28 is larger than that as illustrated in FIG. 3. As can be seen from the comparison of FIGS. 3 and 4, the volume of the first storage section 21 is reduced when the bellows structure 28 contracts and deforms, and thus the volume of the blood reservoir 20 is reduced. The amount of contraction deformation of the bellows structure 28 can be adjusted by adjusting the depth of screwing of the male thread 93 into the female thread 83, which in turn can adjust the volume of the blood reservoir 20. The support member 90 is displaced together with the upper wall 21a of the first storage section 21, and the bottom cap 80 has the bottom 80b that comes into contact with the bottom 21b of the first storage section 21. Accordingly, the male thread 93 of the support member 90 and the female thread 83 of the bottom cap 80 constitute a bellows adjustment mechanism for adjusting the amount of expansion or contraction of the bellows structure 28. The bottom cap 80 or the support member 90 may have a scale indicating the rotational position of the bottom cap 80 or the depth of screwing of the male thread 93 into the female thread 83.

The O ring 97 held in the groove 94 of the skirt portion 92 is in contact with the female thread 83 of the bottom cap 80, and is compressed in the radial direction by the support member 90 and the bottom cap 80. The O ring 97 serves to increase the frictional force between the support member 90 and the bottom cap 80, and prevents the relative position of the male thread 93 and the female thread 83 from being changed by the centrifugal force or vibration during centrifugation. This maintains the amount of contraction deformation of the bellows structure 28 constant, and also suppresses an unintentional variation in the volume of the blood reservoir 20.

The support member 90 prevents bending deformation or buckling deformation of the blood reservoir 20 (particularly the third storage section 23) due to the centrifugal force that acts on blood in the blood reservoir 20 during centrifugation. The bottom cap 80 supports both the blood reservoir 20 and the support member 90 via the female thread 83 during centrifugation. Therefore, it is preferable that the support member 90 and the bottom cap 80 have a mechanical strength high enough for them to be considered as substantially rigid bodies. It is also preferable that the support member 90 and the bottom cap 80 have transparency so that the blood stored in the blood reservoir 20 can be seen through the support member 90 and the bottom cap 80, which have been attached to the blood reservoir 20 (see FIG. 1). In view of the above, examples of the materials for the support member 90 and the bottom cap 80 include resin materials such as polycarbonate, polypropylene, rigid polyvinyl chloride, polyoxymethylene, and polyether ether ketone.

The materials for the O ring 97 are not particularly limited and may be materials having rubber elasticity (also referred to as elastomers), e.g., rubber such as natural rubber, isoprene rubber, and silicone rubber, or thermoplastic elastomers such as styrene elastomer, olefin elastomer, and polyurethane elastomer. Instead of the O ring 97, any of the above materials may be embedded in the support member 90 or the bottom cap 80 by coinjection molding so as to increase the frictional force between the support member 90 and the bottom cap 80.

When the bottom cap 80 has transparency, the O ring 97 attached to the skirt portion 92 can be seen through the bottom cap 80. Therefore, the bottom cap 80 may have a plurality of marks 98 on the outer circumferential surface for positioning of the O ring 97. Each of the marks 98 may be provided with a hematocrit value of blood (which is omitted from the drawings). The vertical positions of the marks 98, each indicating a hematocrit value, are designed so that the buffy coat will be aligned with the third storage section 23 when blood having the indicated hematocrit value is centrifuged. The hematocrit value of blood is determined before centrifugation, and the bottom cap 80 is rotated to adjust the amount of contraction deformation of the bellows structure 28 so that the O ring 97 is positioned at the mark 98 corresponding to the hematocrit value obtained (see FIGS. 3 and 4). Thus, the operation of adjusting the volume of the blood reservoir 20 in accordance with blood can be easily and quickly performed. Any position on the support member 90 (particularly the skirt portion 92) other than the O ring 97 may be seen through the bottom cap 80 to adjust the amount of contraction deformation of the bellows structure 28.

[Method of Use]

A method of use of the device 1 will be described.

First, blood (bone marrow fluid) that is to be centrifuged is collected. Any collection method may be used. For example, a syringe previously moistened with heparin may be inserted into more than a dozen sites of bone marrow to draw out a predetermined volume (e.g., about 100 ml to 400 ml) of the bone marrow fluid.

Next, a blood volume and a hematocrit value of the collected blood are measured. Then, a red blood cell volume and a plasma volume are calculated from the blood volume and the hematocrit value.

The empty device 1 is prepared. The bottom cap 80 is rotated to adjust the amount of contraction deformation of the bellows structure 28. The amount of contraction deformation is determined based on the previously calculated red blood cell volume and plasma volume so that the buffy coat will be formed within the third storage section 23 of the blood reservoir 20 after centrifugation. When the bottom cap 80 has the marks 98 indicating the hematocrit values of blood, the bottom cap 80 is rotated to position the O ring 97 at the mark 98 corresponding to the measured hematocrit value of the blood. In this case, the calculation of the red blood cell volume and the plasma volume is not necessary.

Next, the collected blood is injected into the blood reservoir 20 via the mouth 24. Then, the top cap 25 is fitted on the mouth 24, and the mouth 24 is liquid-tightly sealed.

Subsequently, the device 1 filled with blood is mounted in a centrifuge, followed by centrifugation. The centrifugal force acts parallel to the central axis 1a in the direction of the arrow F in FIGS. 1 and 3. The blood is centrifugally separated into red blood cell components in the first storage section 21, plasma components in the second storage section 22, and the buffy coat (white blood cell components and platelets) in the third storage section 23. In order for the buffy coat to be properly located in the third storage section 23, the fine adjustment of the vertical position of the buffy coat may be made as needed by rotating the bottom cap 80 after centrifugation.

[Effects]

In this embodiment, the first storage section 21 has the bellows structure (volume adjustment mechanism) 28. The amount of contraction of the bellows structure 28 is adjusted in accordance with the blood volume and the hematocrit value of blood to be centrifuged, so that the volume of the blood reservoir 20 can be adjusted. Thus, even if each blood injected into the blood reservoir 20 differs from one another in the blood volume and the hematocrit value, the position of the buffy coat after centrifugation can always be aligned with the third storage section 23. Consequently, the rate of collection of white blood cell components can be improved.

The amount of contraction of the bellows structure 28 can be adjusted by adjusting the depth of screwing of the male thread 93 into the female thread 83. The male thread 93 and the female thread 83 constitute the bellows adjustment mechanism. Both the bellows structure 28 and the bellows adjustment mechanism are very simple in configuration, and therefore can achieve high reliability, high durability, and low cost. Moreover, it is easy to make the fine adjustment of the amount of contraction of the bellows structure 28, and further to make the fine adjustment of the volume of the blood reservoir 20.

Since the blood reservoir 20 is made of materials having the shape retention properties, the buffy coat is not likely to mix with a layer of red blood cells or a layer of blood plasma, even if the fine adjustment of the amount of contraction of the bellows structure 28 is made by rotating the bottom cap 80 after centrifugation.

The bellows structure 28 is formed as a part of the blood reservoir 20. Therefore, the presence of the bellows structure 28 results in only a slight decrease in the volume of the blood reservoir 20.

The first storage section 21 that stores red blood cell components after centrifugation has the bellows structure 28. Therefore, the buffy coat is easily located in the third storage section 23 after centrifugation. This is advantageous to further improve the rate of collection of white blood cell components.

In the actual operation of centrifugation of blood, the white blood cell components in the third storage section 23 are taken out of the blood reservoir 20 after centrifugation. To ensure the efficient collection of the white blood cell components while reducing the mixing of other components, it is desirable that the white blood cell components in the third storage section 23 are poured out of the blood reservoir 20 while the communications between the third storage section 23 and each of the first storage section 21 and the second storage section 22 are blocked. The configuration of the blood component separation device having a structure that is capable of performing this process is not particularly limited, and various configurations may be employed. Hereinafter, typical embodiments will be illustratively described.

(Embodiment 2)

In Embodiment 2, a blood component separation device including first and second blocking members will be described. The first and second blocking members are movable and block the communication between the third storage section 23 and the first storage section 21 and the communication between the third storage section 23 and the second storage section 22, respectively.

[Configuration of Blood Component Separation Device]

Figure 5:
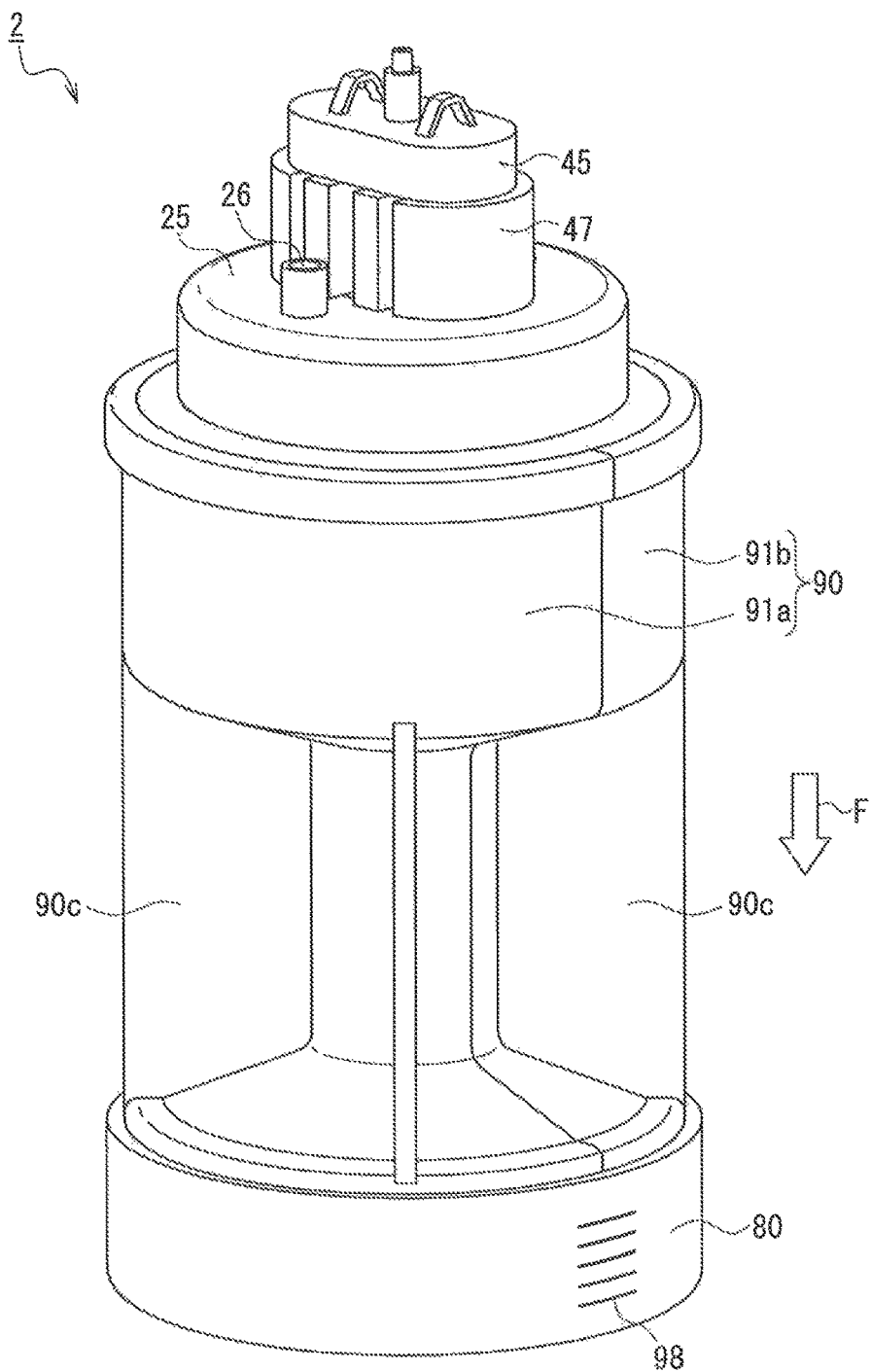
FIG. 5 is a perspective view of a blood component separation device of Embodiment 2 of the present invention.
Figure 6:
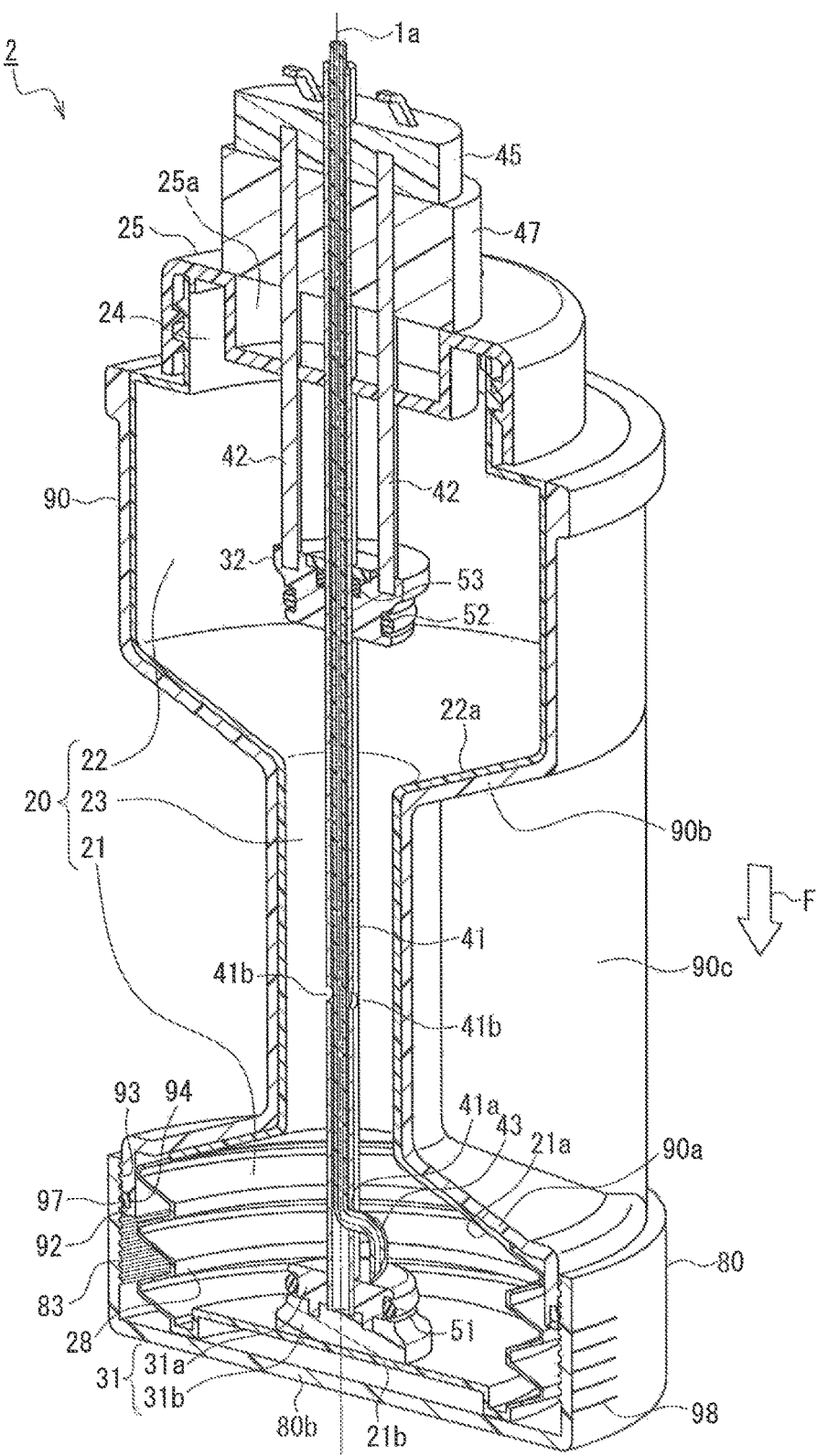
FIG. 6 is a cross-sectional perspective view of a blood component separation device of Embodiment 2 of the present invention.

FIG. 5 is a perspective view of a blood component separation device 2 (simply referred to as a "device 2" in the following) of Embodiment 2 of the present invention. FIG. 6 is a cross-sectional perspective view of the device 2. In the following description, the members of the device 2 of Embodiment 2 that are the same as or correspond to those of the device 1 of Embodiment 1 are denoted by the same reference numerals, and the explanation of these members will not be repeated. Hereinafter, the device 2 of Embodiment 2 will be described mainly in terms of differences from the device 1 of Embodiment 1.

As illustrated in FIG. 6, a first disk-like blocking member 31 is provided inside the first storage section 21. A first O ring 51 is attached to the outer circumferential surface (cylindrical surface) of the first blocking member 31. The first blocking member 31 is held at the lower end of a first hollow cylindrical rod 41. The first rod 41 extends upward along the central axis 1*a* and penetrates the top cap 25. The first rod 41 has a first hole 41*a* and a plurality of (e.g., two in this embodiment) second holes 41*b* in the cylindrical outer wall. The first hole 41*a* and the two second holes 41*b* connect the inside of the first rod 41 to the outside. The first hole 41*a* is provided in the vicinity of and slightly above the first blocking member 31. The second holes 41*b* are provided so as to be near the upper end of the third storage section 23 when the first blocking member 31 is located in the position where the communication between the first storage section 21 and the third storage section 23 is blocked (see FIGS. 9 and 10 as described later).

A hollow cylindrical soft tube 43 is inserted into the first rod 41. The lower end of the tube 43 passes through the first hole 41*a* and out of the first rod 41. The tube 43 that is drawn from the first rod 41 is bent downward, and the opening of the lower end of the tube 43 is located in the vicinity of the upper surface of the first blocking member 31.

The upper end of the tube 43 is drawn from the opening of the upper end of the first rod 41. Although not illustrated, the upper end of the tube 43 is provided with a connector (female connector) that can be connected to the mouth (male luer) of a syringe.

The outer diameter of the tube 43 is smaller than the inner diameter of the first rod 41. Therefore, a slight gap is formed between the first rod 41 and the tube 43 in the first rod 41.

A second disk-like blocking member 32 is provided inside the second storage section 22. A second O ring 52 is attached to the outer circumferential surface (cylindrical surface) of the second blocking member 32. The second blocking member 32 is held at the lower ends of two second rods 42. The second rods 42 are arranged symmetrically with respect to the first rod 41, extend upward parallel to the first rod 41, and penetrate the top cap 25. The upper ends of the second rods 42 are secured by an operating piece 45 that is provided above the top cap 25.

The first rod 41 passes through the second blocking member 32 and the operating piece 45. In order to form a liquid-tight seal between the outer circumferential surface of the first rod 41 and the second blocking member 32, a third O ring 53 is attached to the inner circumferential surface of a through hole, through which the first rod 41 passes, in the second blocking member 32.

It is preferable that the materials for the first blocking member 31 and the second blocking member 32 are hard enough for them to be considered as substantially rigid bodies so that the O rings 51, 52, 53 can form a liquid-tight seal. Moreover, it is preferable that the second blocking member 32 is made of materials with a low specific gravity to avoid being affected by large centrifugal force during centrifugation. The specific gravity of the materials for the second blocking member 32 is preferably lower than the specific gravity (about 1.027) of blood plasma. In view of the above, examples of the materials for the first blocking member 31 and the second blocking member 32 include resin materials such as polypropylene (PP), polyethylene (PE), and ethylene-vinyl acetate copolymer resin (EVA). In order to suppress the adhesion of red blood cells to the first blocking member 31 and the second blocking member 32, it is preferable that the upper surfaces of the first blocking member 31 and the second blocking member 32 are inclined surfaces such as circular conical surfaces, or are covered with a coating. In Embodiment 2, the first blocking member 31 includes a portion 31*a* that holds the O ring 51 and a large-diameter portion 31*b* that is under the portion 31*a* and has a relatively large diameter compared to the portion 31*a*. The large-diameter portion 31*b* is made of soft materials with flexibility rather than the hard materials as described above. This is because in the assembly operation of the device 2, since the blood reservoir 20 is integrally molded, the first blocking member 31 needs to be inserted through the third storage section 23 from the second storage section 22 and to be placed in the first storage section 21.

On the other hand, the O rings 51, 52, 53 may be general-purpose O rings that can form a liquid-tight seal. The materials for the O rings 51, 52, 53 are not particularly limited and may be materials having rubber elasticity (also referred to as elastomers), e.g., rubber such as natural rubber, isoprene rubber, and silicone rubber, or thermoplastic elastomers such as styrene elastomer, olefin elastomer, and polyurethane elastomer.

The first rod 41 protruding outside the blood reservoir 20 is operable to move the first blocking member 31 and the first rod 41 up and down in combination. The operating piece 45 securing the upper ends of the second rods 42 is operable to move the second blocking member 32, the second rods 42, and the operating piece 45 up and down in combination. The up-and-down movement of the combined parts including the first blocking member 31 can be independent of the up-and-down movement of the combined parts including the second blocking member 32.

A stopper 47 is inserted into the space between the top cap 25 and the operating piece 45. The stopper 47 has three notches 47*n*, each of which extends in the vertical direction (see FIG. 8 as will be described later). The three notches 47*n* receive the first rod 41 and the two second rods 42. The stopper 47 restricts the downward movement of the combined parts including the second blocking member 32, the second rods 42, and the operating piece 45. The stopper 47 can be freely inserted into and extracted from the space between the top cap 25 and the operating piece 45 by shifting the stopper 47 in the horizontal direction along the notches 47*n*.

In FIG. 6, the lower surface of the first blocking member 31 is in contact with the bottom 21*b* of the first storage section 21. The second blocking member 32 is hanging in the second storage section 22 and does not come into contact with the inner circumferential surface of the second storage section 22. In the present invention, the positions of the first blocking member 31 and the second blocking member 32 as illustrated in FIG. 6 are called "initial positions".

In Embodiment 2, the upper surface of the top cap 25 has a cavity 25a, into which the operating piece 45 is to be fitted. The stopper 47 is larger than the opening of the cavity 25a, and therefore does not fall in the cavity 25a.

An injection port 26 and a vent filter 27 (see FIG. 8) are provided in the region outside the cavity 25a in the upper surface of the top cap 25. Unlike Embodiment 1, blood is injected into the blood reservoir 20 via the injection port 26. The vent filter 27 allows the flow of gas but prevents the flow of liquid, and also filters out bacteria or the like. The vent filter 27 closes a through hole (not illustrated) formed in the top cap 25. There is a gaseous communication between the blood reservoir 20 and the outside via the vent filter 27. When blood is injected into the empty blood reservoir 20, air that is originally present in the blood reservoir 20 is discharged from the blood reservoir 20 to the outside via the vent filter 27. This suppresses an excessive increase in the pressure in the blood reservoir 20 and thus makes it possible to inject a desired volume of blood into the blood reservoir 20 without reducing the injection rate of the blood into the blood reservoir 20. In this embodiment, the injection port 26 and the vent filter 27 are provided in the upper surface of the top cap 25. However, the positions of the injection port 26 and the vent filter 27 are not limited thereto. For example, the injection port 26 and the vent filter 27 may be provided in the upper surface of the second storage section 22. Once the vent filter 27 becomes wet with blood, the air permeability of the vent filter 27 will be reduced. Therefore, the vent filter 27 is preferably provided in a location where it is not likely to come into contact with blood.

Similarly to Embodiment 1, the support member 90 is attached to the outer circumferential surface of the blood reservoir 20. The support member 90 is composed of the support halves 91a, 91b. The shape of the support member 90 in this embodiment slightly differs from that of the support member 90 in Embodiment 1. In Embodiment 2, the support member 90 has a neck along the narrow portion of the third storage section 23. Four ribs 90c extend radially from the neck and join the first support portion 90a and the second support portion 90b. The support member 90 covers almost the entire outer circumferential surface of the second storage section 22. However, the support member 90 may have any shape, and the shape of the support member 90 in this embodiment may be the same as that of the support member 90 in Embodiment 1.

In Embodiment 2, a portion (central portion) of the bottom 21b of the first storage section 21 is spaced away from the bottom 80b of the bottom cap 80 in the upward direction. However, similarly to Embodiment 1, the entire bottom 21b of the first storage section 21 may be in contact with the bottom 80b of the bottom cap 80.

Except for the above, the device 2 is the same as device 1 of Embodiment 1.

[Method of Use]

A method of use of the device 2 will be described.

Blood (bone marrow fluid) that is to be centrifuged is collected in the same manner as Embodiment 1. A blood volume and a hematocrit value of the blood are measured, and then a red blood cell volume and a plasma volume are calculated.

The empty device 2 is prepared, in which the first blocking member 31 and the second blocking member 32 are at the initial positions as illustrated in FIG. 6. The bottom cap 80 is rotated to adjust the amount of contraction deformation of the bellows structure 28 so that the buffy coat will be formed within the third storage section 23 of the blood reservoir 20 after centrifugation. Similarly to Embodiment 1, the amount of contraction deformation may be adjusted by using the marks 98.

Next, the blood is injected into the blood reservoir 20 via the injection port 26. Then, the injection port 26 is liquid-tightly sealed.

Subsequently, the device 2 is mounted in a centrifuge, followed by centrifugation. The centrifugal force acts parallel to the central axis 1a in the direction of the arrow F in FIGS. 5 and 6. The lower surface of the first blocking member 31 is in contact with the bottom surface of the first storage section 21. The stopper 47 is inserted into the space between the top cap 25 and the operating piece 45. Therefore, the vertical positions of the first blocking member 31 and the second blocking member 32 remain unchanged from their initial positions, even if the centrifugal force F acts on them during centrifugation.

After centrifugation, the device 2 is taken out of the centrifuge. The formation of the buffy coat in the third storage section 23 is confirmed. The fine adjustment of the vertical position of the buffy coat may be made as needed by rotating the bottom cap 80.

Figure 7:
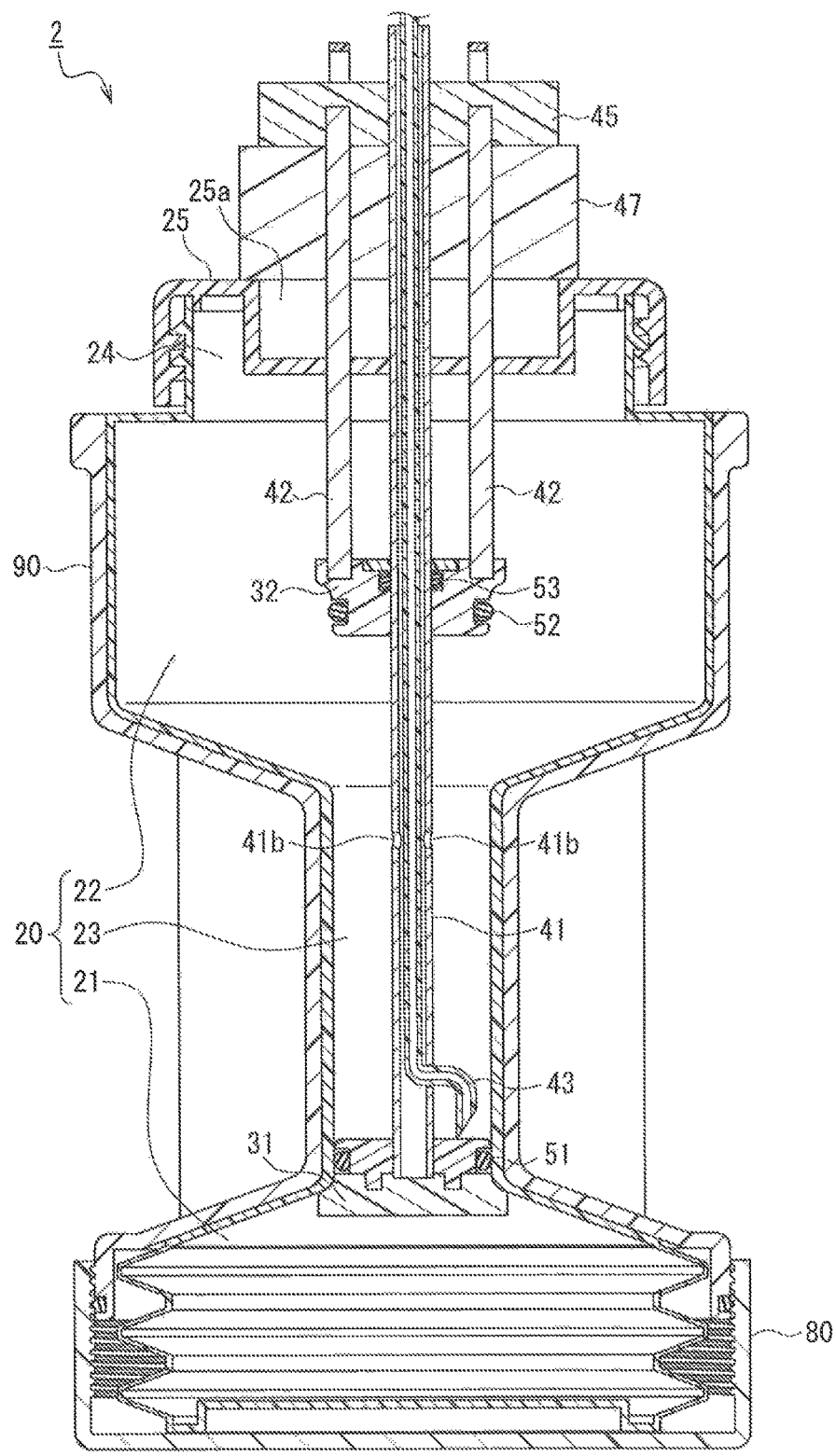
FIG. 7 is a cross-sectional view of a blood component separation device of Embodiment 2 of the present invention, in which the communication between a first storage section and a third storage section is blocked by a first blocking member.

Next, the first rod 41 is pulled up by holding the upper end of the first rod 41 with one hand. At this time, if necessary, the operating piece 45 may be pressed down with the other hand so as to prevent the second blocking member 32 from going up together with the ascending first rod 41. As the first rod 41 is pulled up, the first blocking member 31 attached to the lower end of the first rod 41 moves upward in the first storage section 21. Then, as illustrated in FIG. 7, the first blocking member 31 to which the first O ring 51 is attached is fitted into the lower opening of the third storage section 23. Thus, the first blocking member 31 closes the opening of the third storage section 23 on the first storage section 21 side. Consequently, the communication between the first storage section 21 and the third storage section 23 is liquid-tightly blocked by the first blocking member 31.

Figure 8:
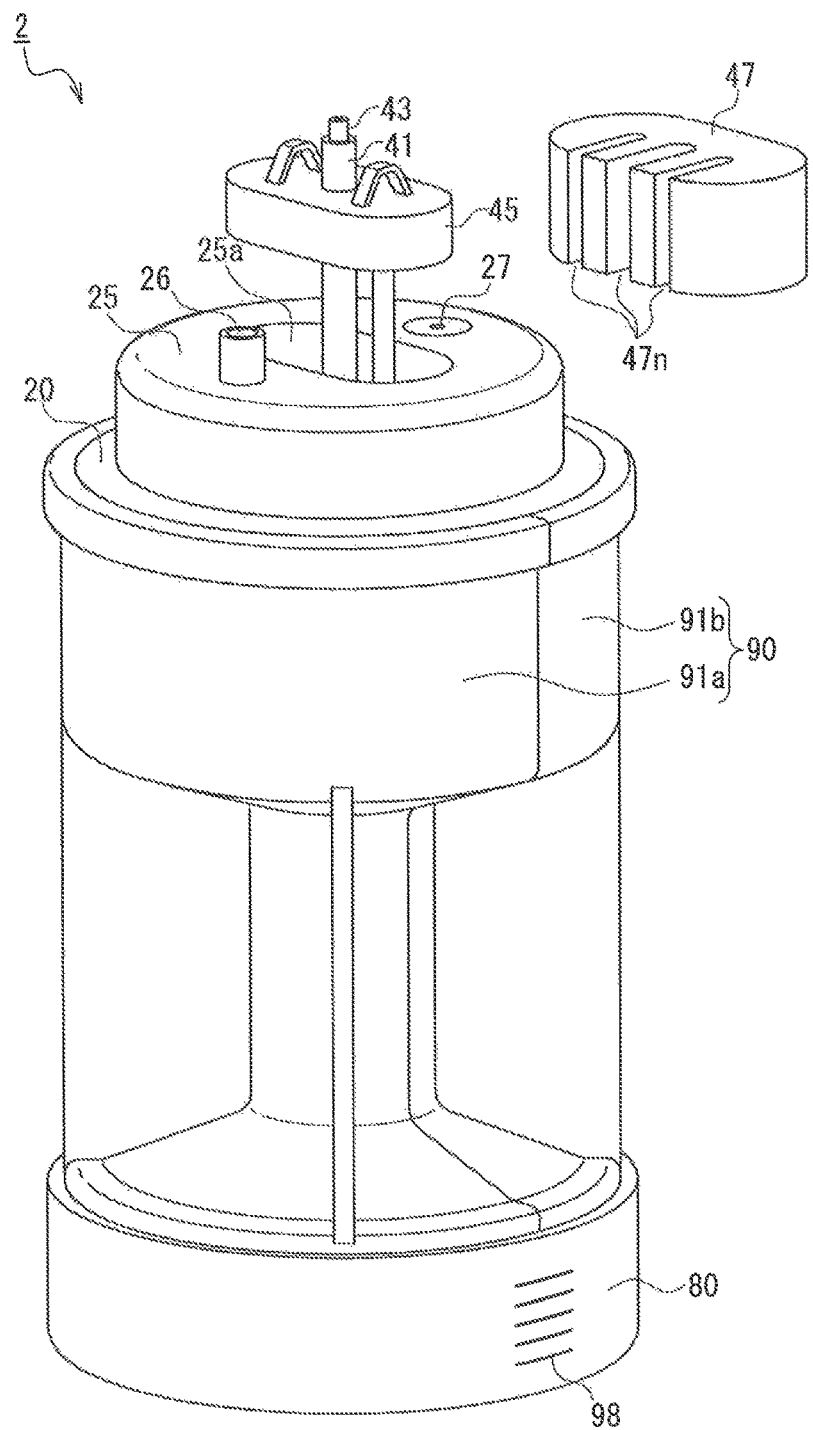
FIG. 8 is a perspective view of a blood component separation device of Embodiment 2 of the present invention, in which a stopper is removed from the state as illustrated in FIG. 7.
Figure 9:
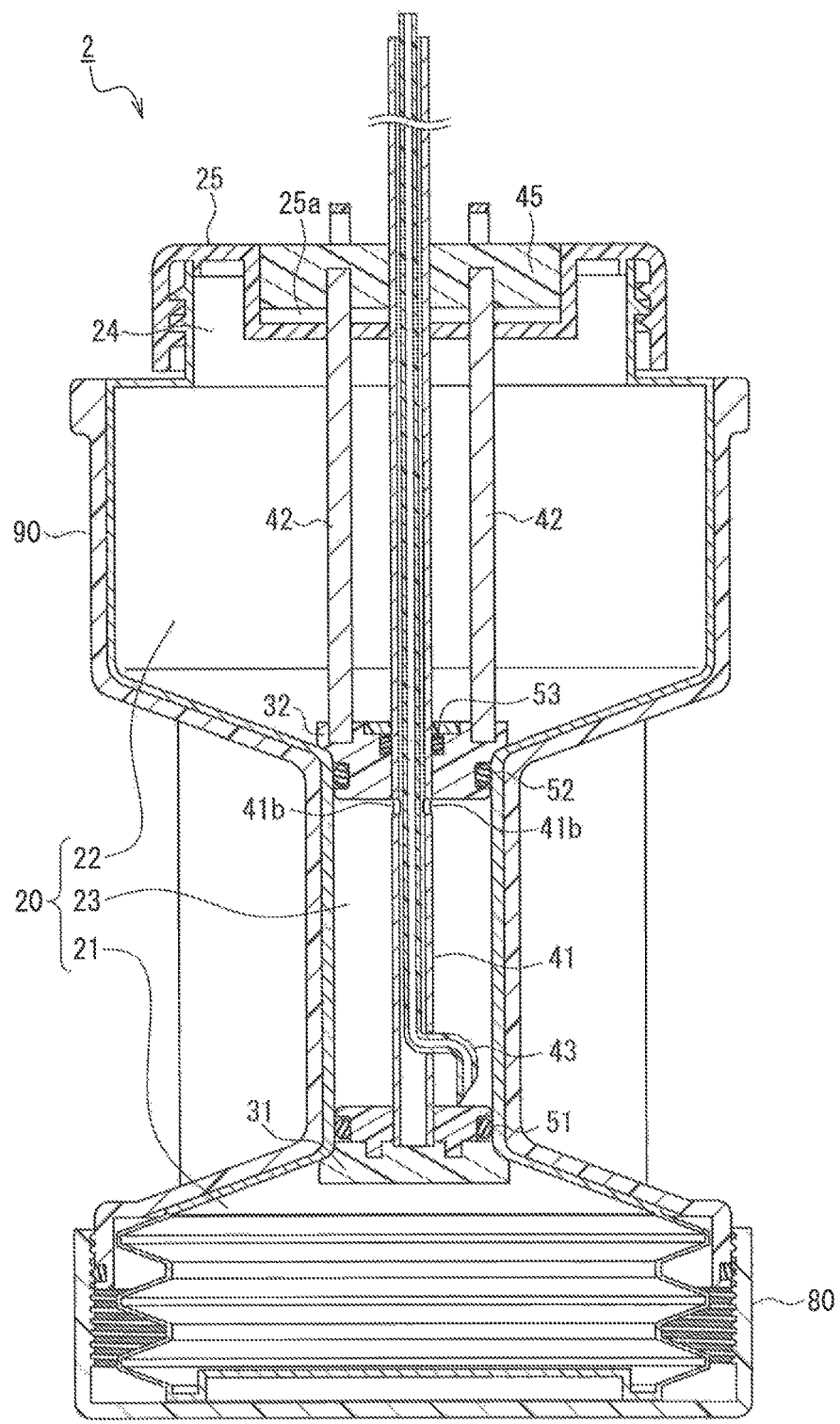
FIG. 9 is a cross-sectional view of a blood component separation device of Embodiment 2 of the present invention, in which the communication between a first storage section and a third storage section is blocked by a first blocking member, and the communication between a second storage section and the third storage section is blocked by a second blocking member.
Figure 10:
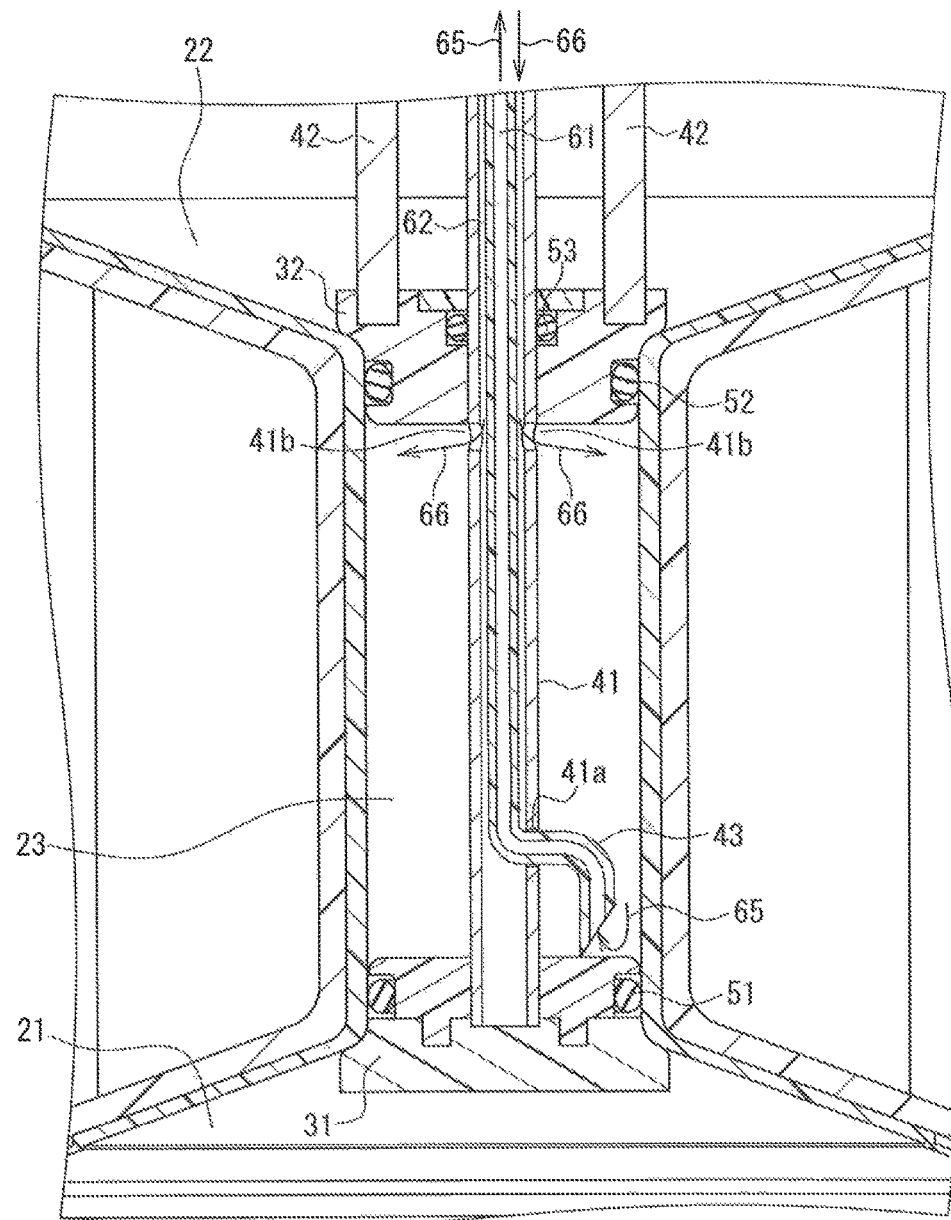
FIG. 10 is an enlarged cross-sectional view illustrating the flow of a fluid when white blood cell components in a third storage section are collected in a blood component separation device of Embodiment 2 of the present invention.

Next, as illustrated in FIG. 8, the stopper 47 is removed from the space between the upper surface of the second storage section 22 and the operating piece 45. Subsequently, the operating piece 45 is pressed down with one hand. At this time, if necessary, the upper end of the first rod 41 may be pulled upward with the other hand so as to prevent the first blocking member 31 from going down together with the descending operating piece 45. As the operating piece 45 is pressed down, the second blocking member 32 attached to the lower ends of the second rods 42 moves downward in the second storage section 22. Then, as illustrated in FIG. 9, the second blocking member 32 to which the second O ring 52 is attached is fitted into the upper opening of the third storage section 23. Thus, the second blocking member 32 closes the opening of the third storage section 23 on the second storage section 22 side. Consequently, the communication between the second storage section 22 and the third storage section 23 is liquid-tightly blocked by the second blocking member 32. The operating piece 45 is fitted into the cavity 25a of the top cap 25.

In this manner, the first storage section 21 in which the red blood cell components have been stored, the third storage section 23 in which the white blood cell components have been stored, and the second storage section 22 in which the plasma components have been stored are liquid-tightly separated from one another. The lower end of the tube 43 that is drawn from the first hole 41a of the first rod 41, and the second holes 41b of the first rod 41 are open to the inside of the third storage section 23.

Next, the mouth (male luer) of an empty syringe is connected to a connector (not illustrated) on the upper end of the tube 43, and a plunger of the syringe is pulled. Thus, the white blood cell components in the third storage section 23 are aspirated and collected into the syringe via a flow path (first flow path) 61 in the tube 43, as indicated by the arrows 65 in FIG. 10. As the white blood cell components move from the third storage section 23 to the syringe, outside air enters the third storage section 23 through a flow path (second flow path) 62 that connects the gap between the first rod 41 and the tube 43, and the second holes 41b of the first rod 41 in sequence, as indicated by the arrows 66 in FIG. 10. Therefore, the pressure in the third storage section 23 does not become excessively negative, and the white blood cell components can be easily collected.

Figure 11:
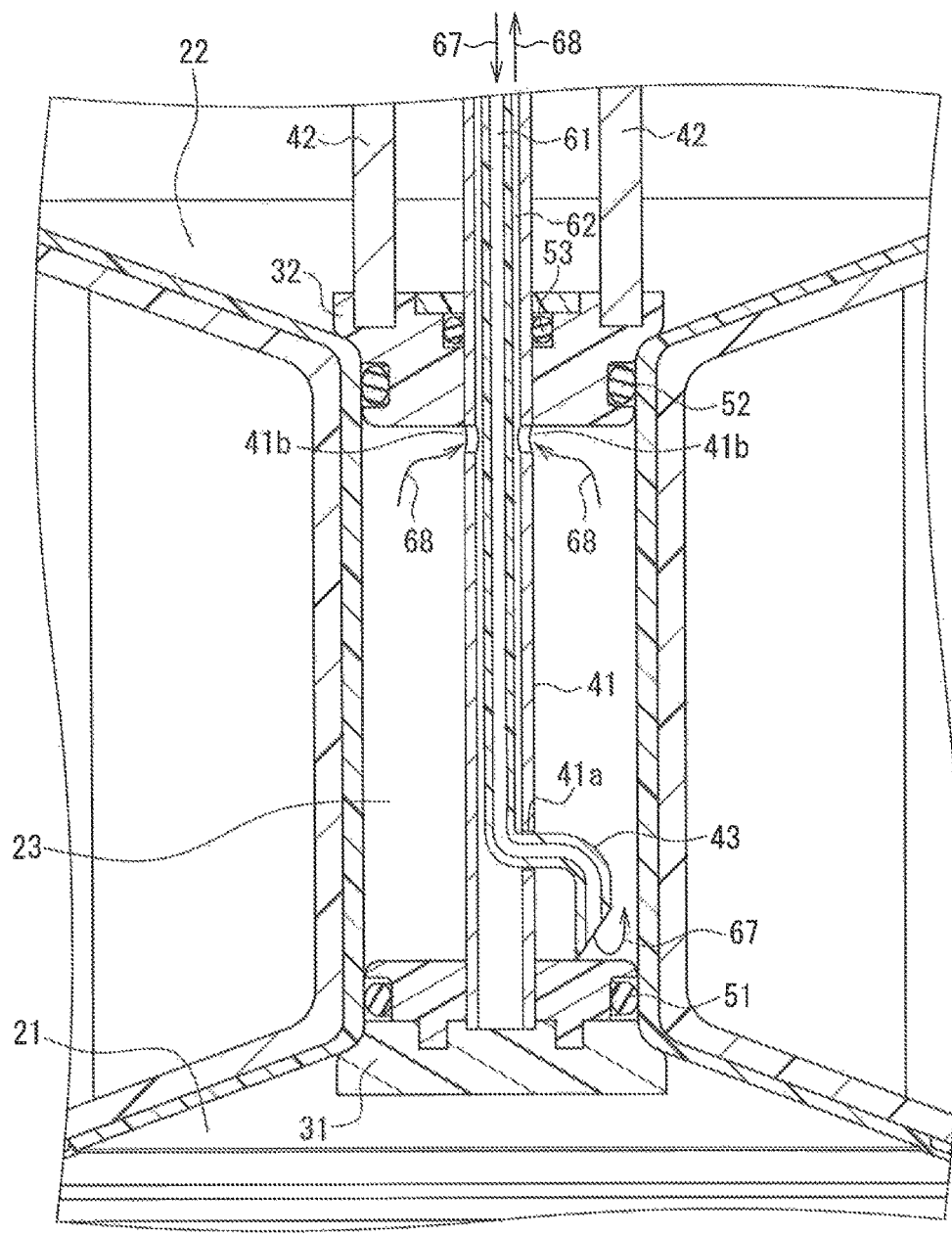
FIG. 11 is an enlarged cross-sectional view illustrating the flow of a fluid when the inside of a third storage section is washed with a physiological saline in a blood component separation device of Embodiment 2 of the present invention.

Moreover, the inside of the third storage section 23 and the tube 43 may be washed with a physiological saline so that the remaining white blood cell components are further collected. This process can be performed in the following manner. The syringe in which the white blood cell components have been collected is removed from the connector on the upper end of the tube 43. Instead of the syringe, a syringe filled with a physiological saline is connected to the connector. Then, this syringe is used to inject the physiological saline into the third storage section 23 via the first flow path 61 in the tube 43, as indicated by the arrows 67 in FIG. 11. At this time, air that is already present in the third storage section 23 flows out of the third storage section 23 through the second flow path 62 that connects the second holes 41b of the first rod 41 and the gap between the first rod 41 and the tube 43 in sequence, as indicated by the arrows 68 in FIG. 11. The physiological saline injected into the third storage section 23 may be collected by aspiration with the syringe attached to the upper end of the tube 43 in the same manner as the collection of the white blood cell components. The collected physiological saline contains the white blood cell components. Therefore, the collected physiological saline may be centrifuged to perform the known process of, e.g., concentrating the white blood cell components.

[Effects]

Embodiment 2 has the following effects in addition to the effects of Embodiment 1.

The device 2 of Embodiment 2 includes the first blocking member 31 in the first storage section 21 and the second blocking member 32 in the second storage section 22. After centrifugation, the first blocking member 31 is moved up to close the boundary portion between the first storage section 21 and the third storage section 23, and the second blocking member 32 is moved down to close the boundary portion between the second storage section 22 and the third storage section 23. Therefore, the inside of the blood reservoir 20 is liquid-tightly divided into three sections after the blood is centrifugally separated into three different components: red blood cell components; plasma components; and white blood cell components. In this state, the white blood cell components in the third storage section 23 can be collected via the first flow path 61. Moreover, the remaining white blood cell components in the third storage section 23 can be collected with the physiological saline via the first flow path 61. Thus, the white blood cell components can be efficiently collected without any mixing of other components (red blood cell components, plasma components, etc.).

In order to close the boundary portion between the first storage section 21 and the third storage section 23 and the boundary portion between the second storage section 22 and the third storage section 23, it is not necessary to deform or squeeze the blood reservoir 20 in those boundary portions. Therefore, the third storage section 23 can have a relatively large inner diameter. Consequently, each of the components can easily pass through the third storage section 23 during centrifugation, so that the blood can be easily separated into three different components. This is advantageous to efficiently collect the white blood cell components. Moreover, this is also advantageous to improve the shape retention properties of the blood reservoir 20 to which the support member 90 is not attached.

The tube 43 is inserted into the first rod 41 that holds the first blocking member 31, thereby providing a double tube structure. The first flow path 61 is formed in the tube 43 (inner tube), and the second flow path 62 is formed between the tube 43 (inner tube) and the first rod 41 (outer tube). Since there are two flow paths 61, 62 for the communication between the third storage section 23, in which both ends are sealed, and the outside of the blood reservoir 20, the white blood cell components in the third storage section 23 can be smoothly collected while variations in the pressure in the third storage section 23 are suppressed. Moreover, the first flow path 61 and the second flow path 62 are formed in the first rod 41 that holds the first blocking member 31. Therefore, the number of parts of the device 1 can be reduced, and thus the configuration of the device 1 can be simplified, compared to the case where the first flow path 61 and the second flow path 62 are formed outside the first rod 41.

Except for the above, Embodiment 2 is the same as Embodiment 1. The description of Embodiment 1 can also be applied to Embodiment 2.

(Embodiment 3)

A blood component separation device 3 (simply referred to as a "device 3" in the following) of Embodiment 3 of the present invention differs from the device 2 of Embodiment 2 in that a pressure release mechanism is provided to prevent the pressure in the third storage section 23 from becoming positive when the openings of both ends of the third storage section 23 are closed. Hereinafter, the device 3 of Embodiment 3 will be described mainly in terms of differences from the device 2 of Embodiment 2.

[Configuration of Blood Component Separation Device]

A configuration of the device 3 of Embodiment 3 will be described with reference to the drawings. In the following drawings, the members of the device 3 of Embodiment 3 that are the same as or correspond to those of the devices 1, 2 of Embodiments 1, 2 are denoted by the same reference numerals, and the explanation of these members will not be repeated.

Figure 12:
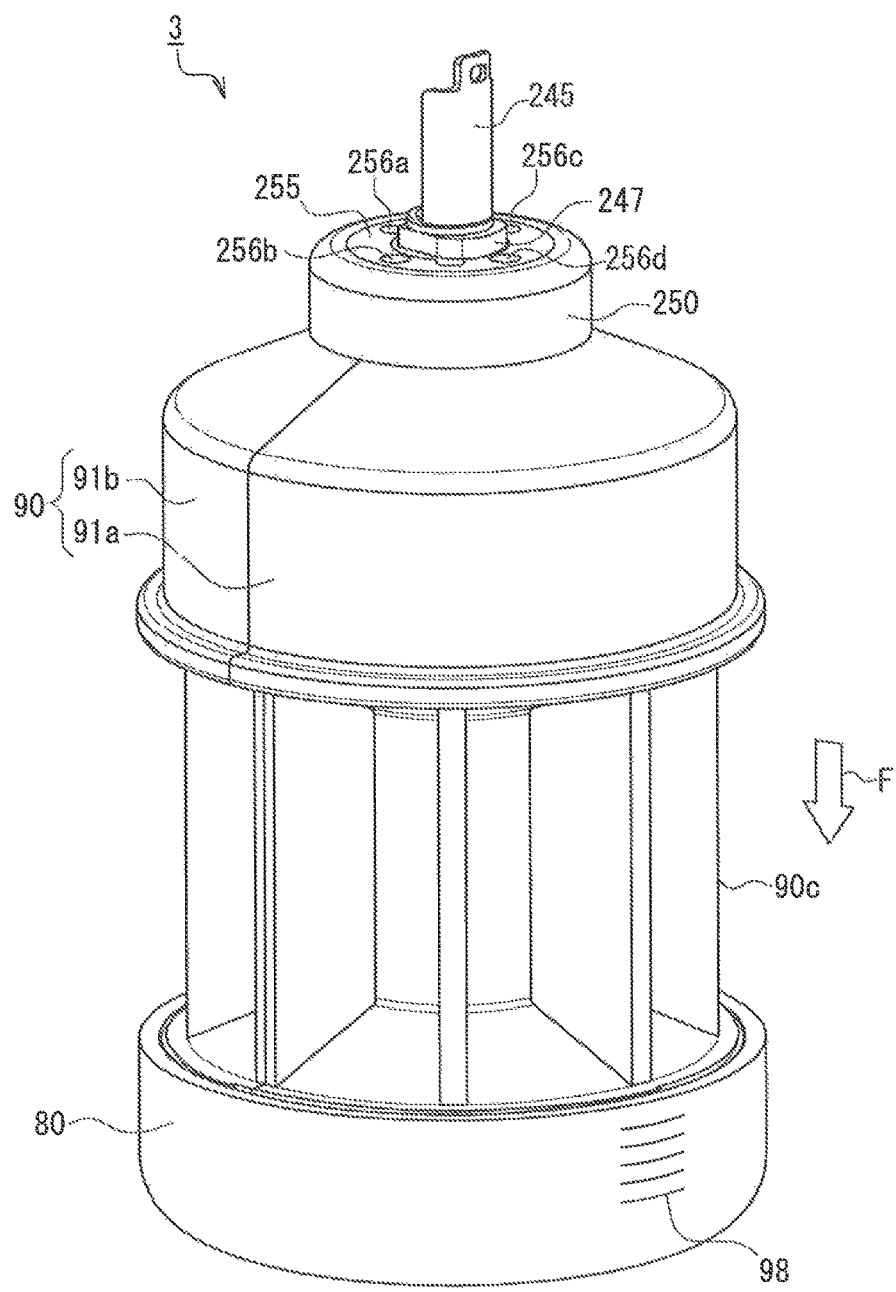
FIG. 12 is a perspective view of a blood component separation device of Embodiment 3 of the present invention.
Figure 13:
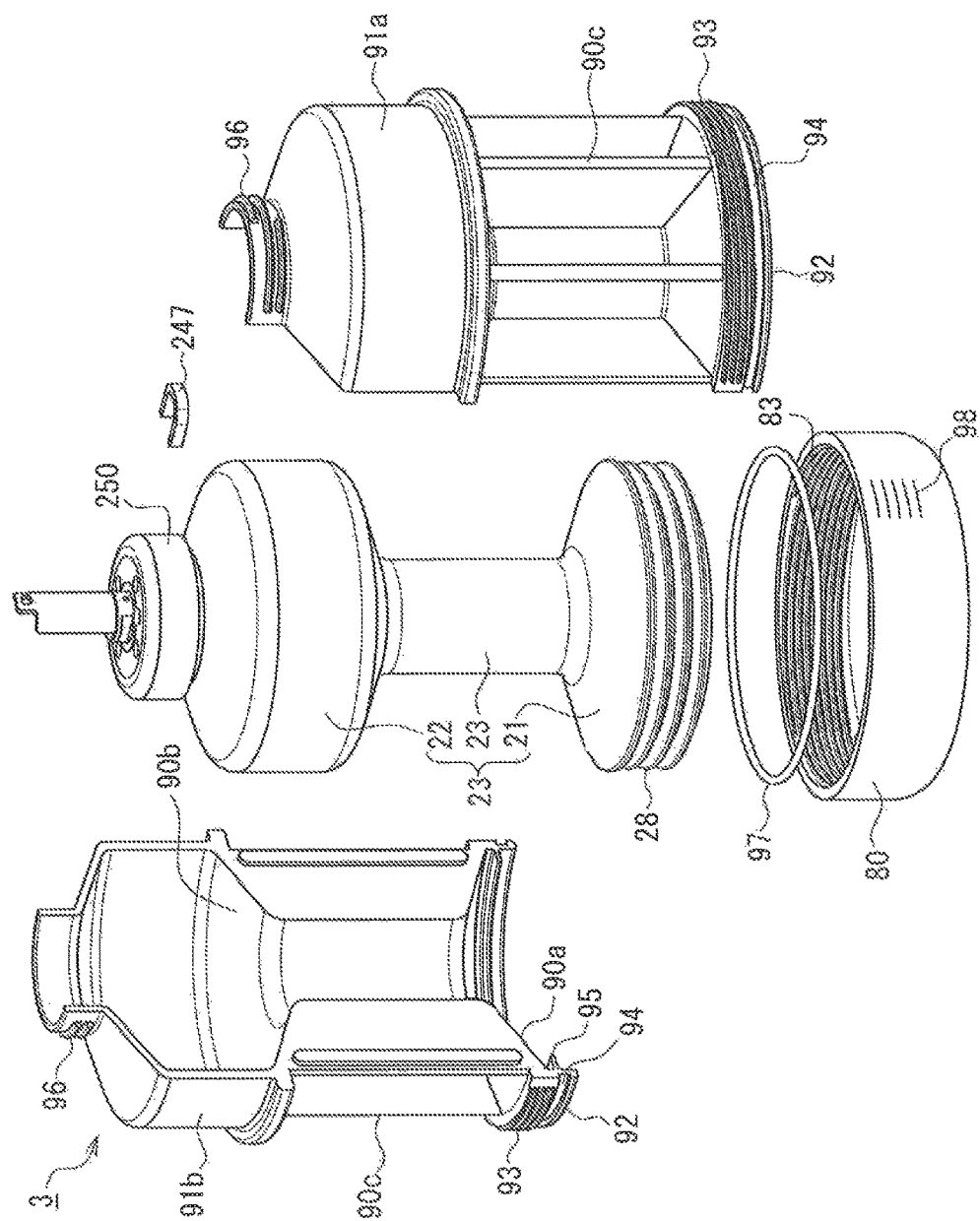
FIG. 13 is an exploded perspective view of a blood component separation device of Embodiment 3 of the present invention.
Figure 14:
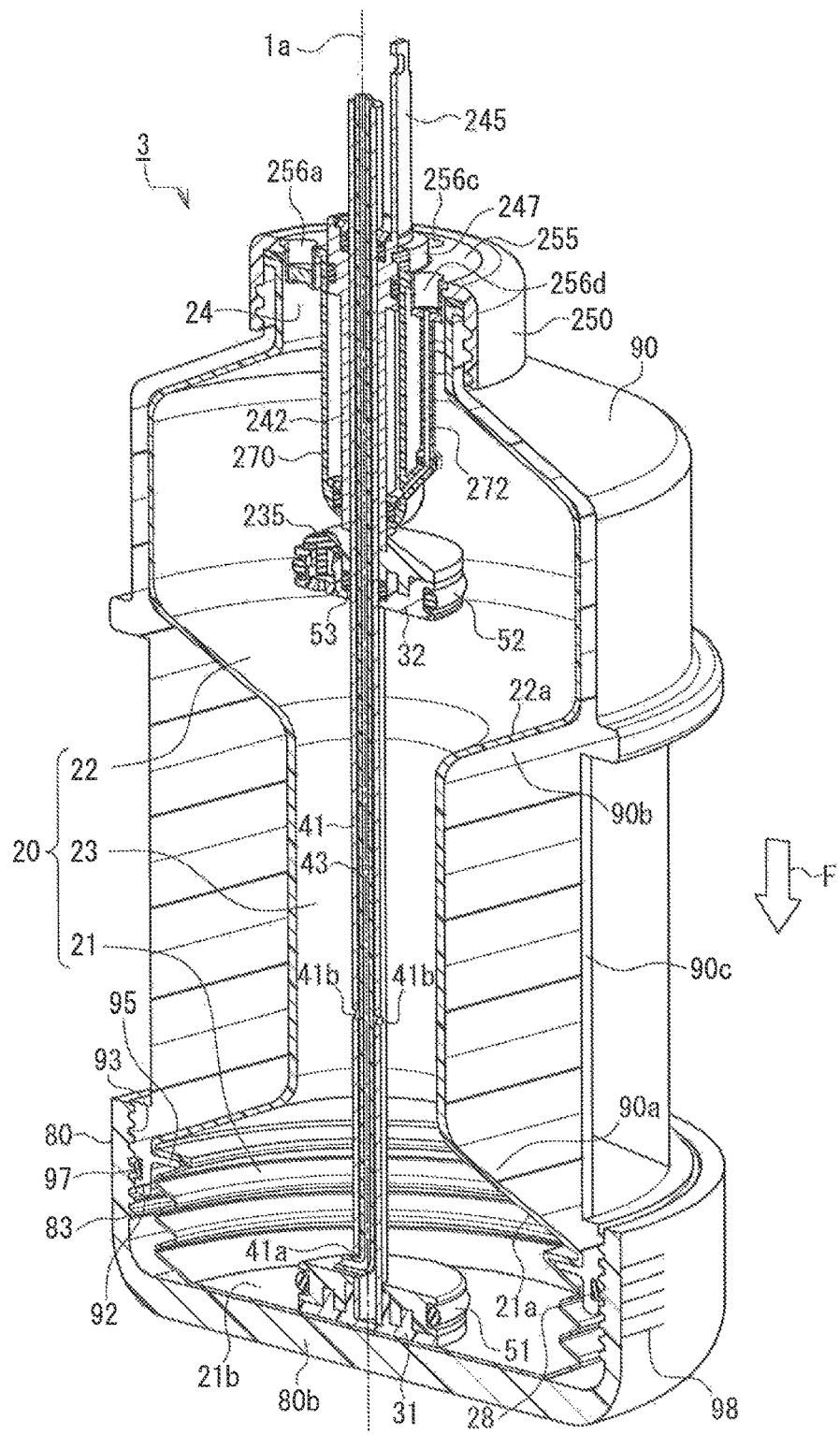
FIG. 14 is a cross-sectional perspective view of a blood component separation device of Embodiment 3 of the present invention.

FIG. 12 is a perspective view of the device 3. FIG. 13 is an exploded perspective view of the device 3. FIG. 14 is a cross-sectional perspective view taken along the longitudinal direction of the device 3. In FIG. 14, an alternate long and short dash line la is a central axis of the device 3.

Similarly to Embodiments 1, 2, the blood reservoir 20 includes the first storage section 21, the second storage section 22, and the third storage section 23 provided between the first storage section 21 and the second storage section 22. The first storage section 21 has the bellows structure 28 on the outer circumferential surface. The bellows structure 28 is able to expand and/or contract in the vertical direction.

Similarly to Embodiments 1, 2, the support member 90 is attached to the outer circumferential surface of the blood reservoir 20. The support member 90 is composed of the support halves 91a, 91b. The shape of the support member 90 in this embodiment slightly differs from those of the support members 90 in Embodiments 1, 2. In Embodiment 3, the support member 90 has the inner circumferential surface substantially along the outer circumferential surface of the blood reservoir 20. The support member 90 covers the blood reservoir 20 from the mouth 24 of the upper end of the blood reservoir 20 to the bellows structure 28. The support half 91a and the support half 91b are joined together with the attachment of a top cap 250 and the bottom cap 80 to their upper and lower ends, respectively (as will be described in detail later).

The support member 90 has a neck along the narrow portion of the third storage section 23, and eight ribs 90c extend radially from the neck. The ribs 90c join the first support portion 90a and the second support portion 90b, and prevent bending deformation or buckling deformation of the support member 90 due to the centrifugal force during centrifugation. The first support portion 90a is in contact with the upper wall 21a of the first storage section 21, and the second support portion 90b is in contact with the lower wall 22a of the second storage section 22.

Similarly to Embodiments 1, 2, the support member 90 has the skirt portion 92 on the lower end. The male thread 93 of the skirt portion 92 is screwed into the female thread 83 of the bottom cap 80. The male thread 93 of the support member 90 and the female thread 83 of the bottom cap 80 constitute the bellows adjustment mechanism for adjusting the amount of expansion or contraction of the bellows structure 28.

As illustrated in FIG. 14, the first disk-like blocking member 31 is provided inside the first storage section 21. The first O ring 51 is attached to the outer circumferential surface of the first blocking member 31. The first blocking member 31 is held at the lower end of the first hollow cylindrical rod 41. The first rod 41 extends upward along the central axis 1a and reaches the outside of the blood reservoir 20. The first rod 41 has the first hole 41a and a plurality of (e.g., two in this embodiment) second holes 41b in the cylindrical outer wall. The first hole 41a and the two second holes 41b connect the inside of the first rod 41 to the outside.

The hollow cylindrical soft tube 43 is inserted into the first rod 41. The lower end of the tube 43 passes through the first hole 41a and out of the first rod 41. The lower end of the tube 43 is open in the vicinity of the upper surface of the first blocking member 31.

Figure 15:
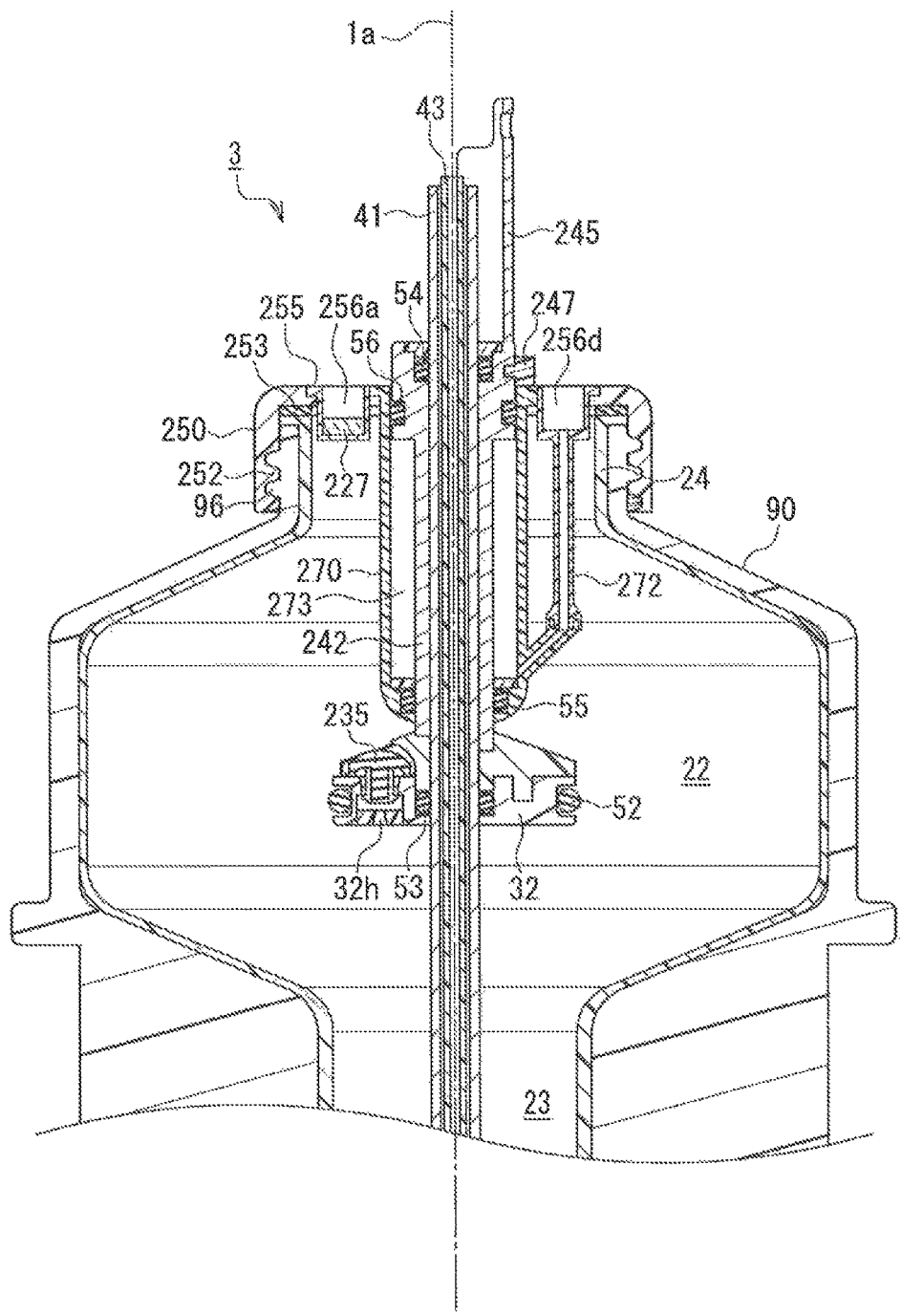
FIG. 15 is an enlarged cross-sectional view of a second blocking member and its periphery in a blood component separation device of Embodiment 3 of the present invention.

The second disk-like blocking member 32 is provided inside the second storage section 22. FIG. 15 is an enlarged cross-sectional view of the second blocking member 32 and its periphery. The second O ring 52 is attached to the outer circumferential surface of the second blocking member 32. The second blocking member 32 is held at the lower end of a second rod (slider) 242. The second rod 242 has a hollow cylindrical shape and is coaxially arranged with the central axis 1a.

The second blocking member 32 has a through hole 32h in the position away from the center. The through hole 32h penetrates the second blocking member 32 in the vertical direction. The through hole 32h is provided with a one-way valve 235. The one-way valve 235 allows a liquid (blood) to flow upward through the through hole 32h, but does not allow it to flow downward through the through hole 32h. In this embodiment, the one-way valve 235 is an umbrella value that has a substantially mushroom shape and is made of materials having rubber elasticity (so-called elastomers). Any type of the one-way value 235 can be used as long as it has the above function. For example, a duckbill valve may be used.

The first rod 41 passes through the second blocking member 32 and the second rod 242. The third O ring 53 is attached to the inner circumferential surface of a through hole, through which the first rod 41 passes, in the second blocking member 32. The third O ring 53 forms a liquid-tight seal between the outer circumferential surface of the first rod 41 and the second blocking member 32. Moreover, a fourth O ring 54 is attached to the inner circumferential surface of the second rod 242 and located in the vicinity of the upper end of the second rod 242. The fourth O ring 54 is provided to seal a gap between the outer circumferential surface of the first rod 41 and the second rod 242.

The second rod 242 is inserted into a hollow cylindrical guide cylinder 270. The upper end of the guide cylinder 270 is held by a substantially disk-like top 255. The top 255 has four ports 256a to 256d (the ports 256b, 256c cannot be seen in FIG. 15). The ports 256a to 256d are through holes that connect the inside of the blood reservoir 20 to the outside. The number of the ports is not limited to four, and may be either larger or smaller than this.

The second rod 242 has an operating piece 245 that extends upward from the portion having the hollow cylindrical shape. The operating piece 245 protrudes above the top 255. Similarly to the operating piece 45 in Embodiment 2, the operating piece 245 is operable to move the second rod 242 and the second blocking member 32 up and down in combination. This up-and-down movement can be independent of the up-and-down movement of the first blocking member 31 and the first rod 41.

A fifth O ring 55 and a sixth O ring 56 are provided to seal a gap between the outer circumferential surface of the second rod 242 and the inner circumferential surface of the guide cylinder 270. The fifth O ring 55 is attached to the inner circumferential surface of the guide cylinder 270 and located in the vicinity of the lower end of the guide cylinder 270. The sixth O ring 56 is attached to the outer circumferential surface of the second rod 242 and located in the vicinity of the upper end of the second rod 242.

A hermetically sealed space 273 which is sealed by the fifth O ring 55 and the sixth O ring 56 is created between the second rod 242 and the guide cylinder 270. The lower end of an air pipe 272 is connected to the portion of the guide cylinder 270 that is located in the vicinity of the lower end of the hermetically sealed space 273. The upper end of the air pipe 272 is connected to the port 256d formed in the top 255. Therefore, the hermetically sealed space 273 communicates with the outside of the blood reservoir 20 via the air pipe 272 and the port 256d. This makes it easy to move the second rod 242 relative to the guide cylinder 270 in the vertical direction without changing the atmospheric pressure in the hermetically sealed space 273.

Similarly to the O rings 51, 52, 53 in Embodiments 1, 2, the O rings 54, 55, 56 may be general-purpose O rings. The materials for the O rings 54, 55, 56 may be the same as those for the O rings 51, 52, 53.

The outer circumferential surface of the second rod 242 is sterilized during the assembly of the device 3. The O rings 55, 56 serve to maintain the sterilized state. This can reduce the possibility that bacteria will enter blood when the second rod 242 is pressed down to close the upper opening of the third storage section 23 with the second blocking member 32 (see FIG. 17 as will be described later).

A substantially U-shaped stopper 247 (see FIG. 13) is removably engaged with the second rod 242 in the horizontal direction. When the second rod 242 is moved up so that the second blocking member 32 is hanging in the second storage section 22 (see FIGS. 14 and 15), the stopper 247 can be engaged with a groove formed on the outer circumferential surface of the second rod 242. In a state where the stopper 247 is engaged with the second rod 242, the lower surface of the stopper 247 is in contact with the upper end of the guide cylinder 270 or the upper surface of the top 255, and thus the second rod 242 cannot be moved down. In the present invention, this state is called a "locked state" by the stopper 247.

The cylindrical mouth 24 of the blood reservoir 20 is surrounded by the support member 90. A male thread 96 is formed on the outer circumferential surface of the portion of the support member 90 that surrounds the mouth 24. The male thread 96 is screwed into a female thread 252 of a top cap 250. An annular sealing member 253 is interposed between the top cap 250 and the edge of the mouth 24 of the blood reservoir 20. The top 255 is fitted into the opening in the center of the top cap 250. Thus, the mouth 24 of the blood reservoir 20 is sealed. In this embodiment, the support member 90 has the male thread 96. However, the present invention is not limited thereto. Similarly to Embodiment 2, the blood reservoir 20 may have the male thread that is screwed into the top cap. Similarly to the top cap 25 in Embodiments 1, 2, the top cap 250 can also serve as a handle that allows the device 2 to be held and carried around with one hand.

The port 256a formed in the top 255 is provided with a vent filter 227 having the same function as that of the vent filter 27 in Embodiment 2. The ports 256b, 256c may be used as blood injection ports for injecting blood into the blood reservoir 20. Each of the blood injection ports may be connected to, e.g., one end of a soft tube. In this case, the other end of the soft tube may be provided with a known female connector.

In FIG. 14, the lower surface of the first blocking member 31 is in contact with the bottom surface of the first storage section 21. The second blocking member 32 is hanging in the second storage section 22 and does not come into contact with the inner circumferential surface of the second storage section 22. The positions of the first blocking member 31 and the second blocking member 32 as illustrated in FIG. 14 are called "initial positions".

[Method of Use]

Using the device 3 having the above configuration, a method for separating collected blood into different blood components by centrifugation will be described.

Blood (bone marrow fluid) that is to be centrifuged is collected in the same manner as Embodiments 1, 2. A blood volume and a hematocrit value of the blood are measured, and then a red blood cell volume and a plasma volume are calculated.

The empty device 3 is prepared, in which the first blocking member 31 and the second blocking member 32 are at the initial positions as illustrated in FIG. 14. The bottom cap 80 is rotated to adjust the amount of contraction deformation of the bellows structure 28 so that the buffy coat will be formed within the third storage section 23 of the blood reservoir 20 after centrifugation. Similarly to Embodiments 1, 2, the amount of contraction deformation may be adjusted by using the marks 98.

Next, the collected blood is injected into the blood reservoir 20 via the blood injection ports 256b, 256c formed in the top 255. Then, the blood injection ports 256b, 256c are liquid-tightly sealed.

Subsequently, the device 3 filled with blood is mounted in a centrifuge, followed by centrifugation. The centrifugal force acts parallel to the central axis 1a in the direction of the arrow F in FIGS. 12 and 14. The lower surface of the first blocking member 31 is in contact with the bottom surface of the first storage section 21. The stopper 247 is engaged with the second rod 242. Therefore, the vertical positions of the first blocking member 31 and the second blocking member 32 remain unchanged from their initial positions, even if the centrifugal force F acts on them during centrifugation.

After centrifugation, the device 3 is taken out of the centrifuge. The formation of the buffy coat in the third storage section 23 is confirmed. The fine adjustment of the vertical position of the buffy coat may be made as needed by rotating the bottom cap 80.

Figure 16:
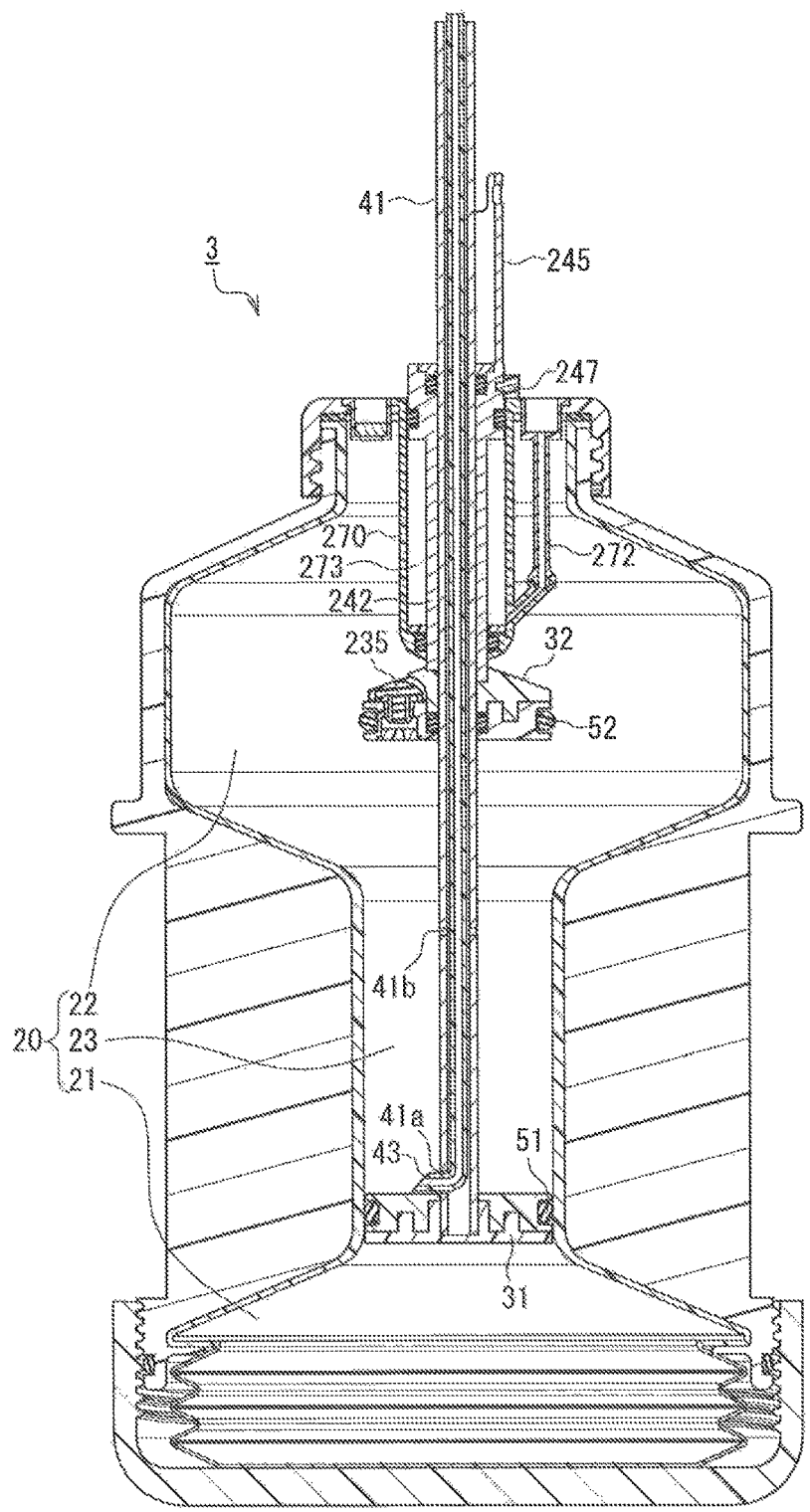
FIG. 16 is a cross-sectional view of a blood component separation device of Embodiment 3 of the present invention, in which the communication between a first storage section and a third storage section is blocked by a first blocking member.

Next, the first rod 41 is pulled up by holding the upper end of the first rod 41. Then, as illustrated in FIG. 16, the first blocking member 31 is fitted into the lower opening of the third storage section 23. Thus, the first blocking member 31 closes the opening of the third storage section 23 on the first storage section 21 side. Consequently, the communication between the first storage section 21 and the third storage section 23 is liquid-tightly blocked by the first blocking member 31. The second blocking member 32 still remains in the initial position (see FIG. 14).

Next, the stopper 247 is removed from the second rod 242 (see FIG. 13). Subsequently, the operating piece 245 is pressed down. As the second rod 242 moves downward, the volume of the hermetically sealed space 273 is reduced. Accordingly, air that is already present in the hermetically sealed space 273 is discharged from the device 3 to the outside through the air pipe 272 and the port 256d. Therefore, the pressure in the hermetically sealed space 273 is not increased, which facilitates the operation of moving the second rod 242 down.

Figure 17:
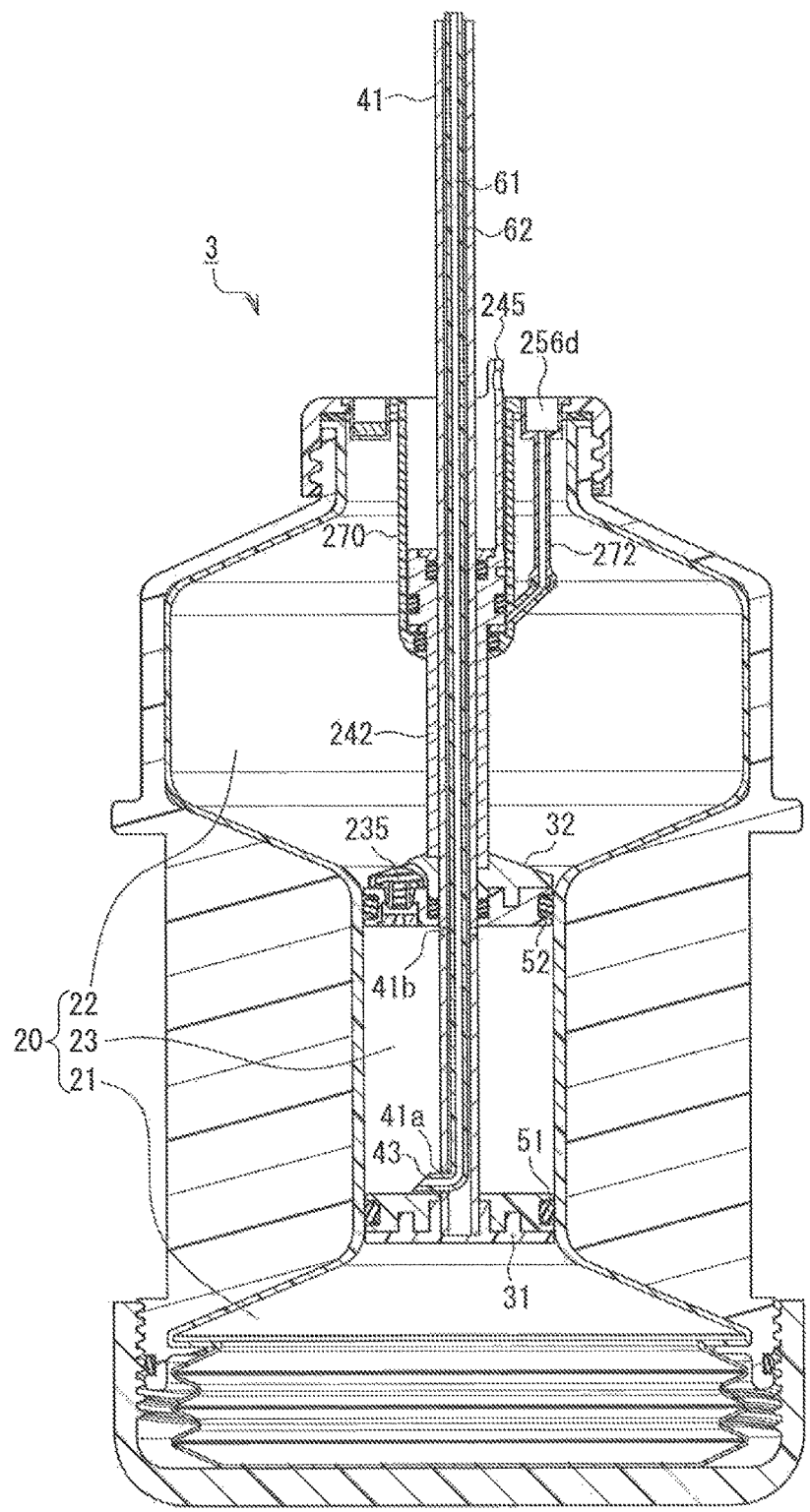
FIG. 17 is a cross-sectional view of a blood component separation device of Embodiment 3 of the present invention, in which the communication between a first storage section and a third storage section is blocked by a first blocking member, and the communication between a second storage section and the third storage section is blocked by a second blocking member.

As illustrated in FIG. 17, the operating piece 245 is operated to fit the second blocking member 32 into the upper opening of the third storage section 23. Thus, the second blocking member 32 closes the opening of the third storage section 23 on the second storage section 22 side. Consequently, the communication between the second storage section 22 and the third storage section 23 is liquid-tightly blocked by the second blocking member 32. The first blocking member 31 has not been displaced from the position as illustrated in FIG. 16.

In this manner, the first storage section 21 in which the red blood cell components have been stored, the third storage section 23 in which the white blood cell components have been stored, and the second storage section 22 in which the plasma components have been stored are liquid-tightly separated from one another. The lower end of the tube 43 that is drawn from the first hole 41a of the first rod 41, and the second holes 41b of the first rod 41 are open to the inside of the third storage section 23.

Thereafter, similarly to Embodiment 2, the white blood cell components in the third storage section 23 are aspirated and collected via the flow path (first flow path) 61 in the tube 43. At the same time, outside air enters the third storage section 23 through the flow path (second flow path) 62 that connects the gap between the first rod 41 and the tube 43, and the second holes 41b of the first rod 41 in sequence.

Moreover, similarly to Embodiment 2, a physiological saline may be injected into the third storage section 23 via the first flow path 61 in the tube 43. Then, the physiological saline is collected via the first flow path 61 in the tube 43. As the physiological saline flows in/out of the third storage section 23 via the first flow path 61, air flows out of/in the third storage section 23 via the second flow path 62. Thus, the remaining white blood cell components in the third storage section 23 and the tube 43 can be collected with the physiological saline.

[Effects]

Embodiment 3 has the following effects in addition to the effects of Embodiment 2.

In Embodiment 3, the second blocking member 32 has the through hole 32h and the one-way valve 235.

In the device 2 of Embodiment 2, the second blocking member 32 does not have the through hole 32h and the one-way valve 235. Therefore, when the lower opening of the third storage section 23 is closed (FIG. 7), and subsequently the second blocking member 32 is being fitted into the upper opening of the third storage section 23, the pressure in the third storage section 23 can be increased. Accordingly, the white blood cell components in the third storage section 23 can pass through the first flow path 61 and/or the second flow path 62 and leak out of the device 2. If the first flow path 61 and the second flow path 62 are sealed, leakage of the white blood cell components from the device 2 can be prevented. In this case, however, an increase in the pressure in the third storage section 23 may cause an accidental situation such that the second blocking member 32 can not be easily fitted into the upper opening of the third storage section 23, or the first blocking member 31 comes off the lower opening of the third storage section 23. The situation may reduce the rate of collection of white blood cell components.

In contrast, Embodiment 3 uses the second blocking member 32 having the through hole 32h and the one-way valve 235. Therefore, when the pressure in the third storage section 23 is increased, the one-way valve 235 opens to allow the white blood cell components in the third storage section 23 to flow through the through hole 32h and into the second storage section 22. The through hole 32h and the one-way valve 235 of the second blocking member 32 function as a pressure release mechanism that releases the pressure in the third storage section 23 to protect the third storage section 23 from abnormally high pressure. Thus, this embodiment can prevent leakage of the white blood cell components to the outside as well as the above malfunctions.

It is also possible to prevent an increase in the pressure in the third storage section 23 in the absence of the one-way valve 235 in the through hole 32h. In this case, however, the third storage section 23 communicates with the second storage section 22 via the through hole 32h, even if there is no need to release the pressure in the third storage section 23. Therefore, when the white blood cell components in the third storage section 23 are aspirated and collected after the first blocking member 31 and the second blocking member 32 close the lower opening and the upper opening of the third storage section 23, respectively (see FIG. 17), the plasma components in the second storage section 22 can flow into the third storage section 23 through the through hole 32h. This reduces the rate of collection of white blood cell components. The one-way valve 235 prevents the flow of the plasma components from the second storage section 22 to the third storage section 23 while the white blood cell components in the third storage section 23 are being collected.

Because of the use of the through hole 32h and the one-way valve 235 in the second blocking member 32, the white blood cell components can flow from the third storage section 23 to the second storage section 22 simultaneously with the release of the pressure in the third storage section 23. However, such a problem of outflow of the white blood cell components due to the presence of the through hole 32h and the one-way valve 235 is negligibly small compared to the significance of the problem of a low collection rate of the white blood cell components caused by leakage of the white blood cell components to the outside of the blood reservoir 20 and the above malfunctions due to the absence of the through hole 32h and the one-way valve 235. Moreover, it is possible to reduce the amount of flow of the white blood cell components through the one-way valve 235 by adjusting the bellows structure 28 so that the buffy coat is formed in the third storage section 23 at the position slightly away from the second storage section 22.

The pressure in the first storage section 21 can be decreased in the process of fitting the first blocking member 31 into the lower opening of the third storage section 23 (see FIG. 16). However, the first storage section 21 in this embodiment has the bellows structure 28. The bellows structure 28 can appropriately deform so that its length is reduced with a decrease in the pressure in the first storage section 21. Therefore, in this embodiment, such a decrease in the pressure in the first storage section 21 is not likely to interfere with the process of fitting the first blocking member 31 into the lower opening of the third storage section 23.

Except for the above, Embodiment 3 is the same as Embodiments 1, 2. The description of Embodiments 1, 2 can also be applied to Embodiment 3.

(Embodiment 4)

A blood component separation device 4 (simply referred to as a "device 4" in the following) of Embodiment 4 of the present invention differs from the device 3 of Embodiment 3 mainly in the following two points. First, in the device 4, the first rod 41 that holds the first blocking member 31 does not have a double tube structure. Second, the device 4 differs from the device 3 in the configuration of the pressure release mechanism that prevents the pressure in the third storage section 23 from becoming positive. Hereinafter, the device 4 of Embodiment 4 will be described mainly in terms of differences from the device 3 of Embodiment 3.

[Configuration of Blood Component Separation Device]

A configuration of the device 4 of Embodiment 4 will be described with reference to the drawings. In the following drawings, the members of the device 4 of Embodiment 4 that are the same as or correspond to those of the devices 1 to 3 of Embodiments 1 to 3 are denoted by the same reference numerals, and the explanation of these members will not be repeated.

Figure 18:
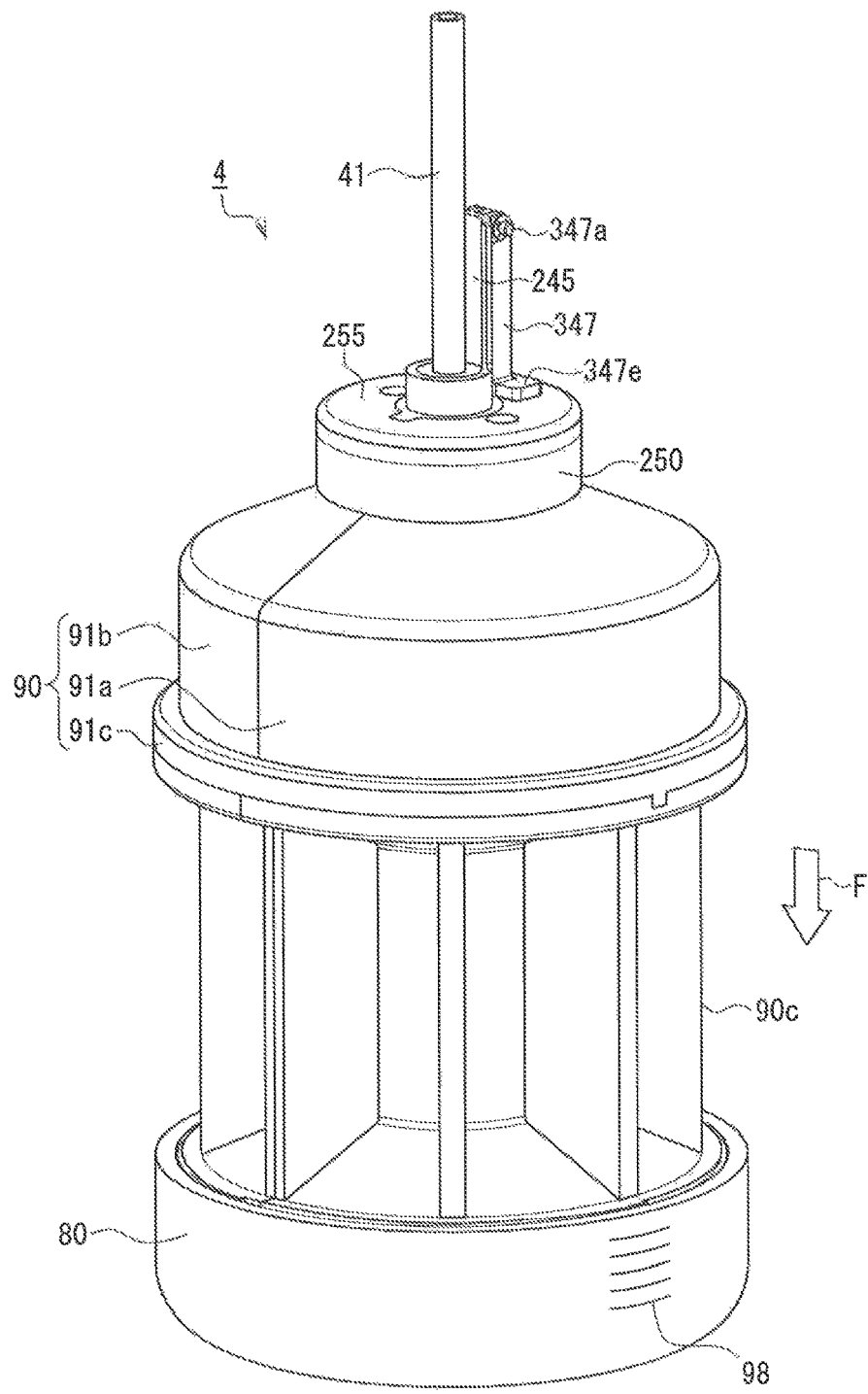
FIG. 18 is a perspective view of a blood component separation device of Embodiment 4 of the present invention.
Figure 19:
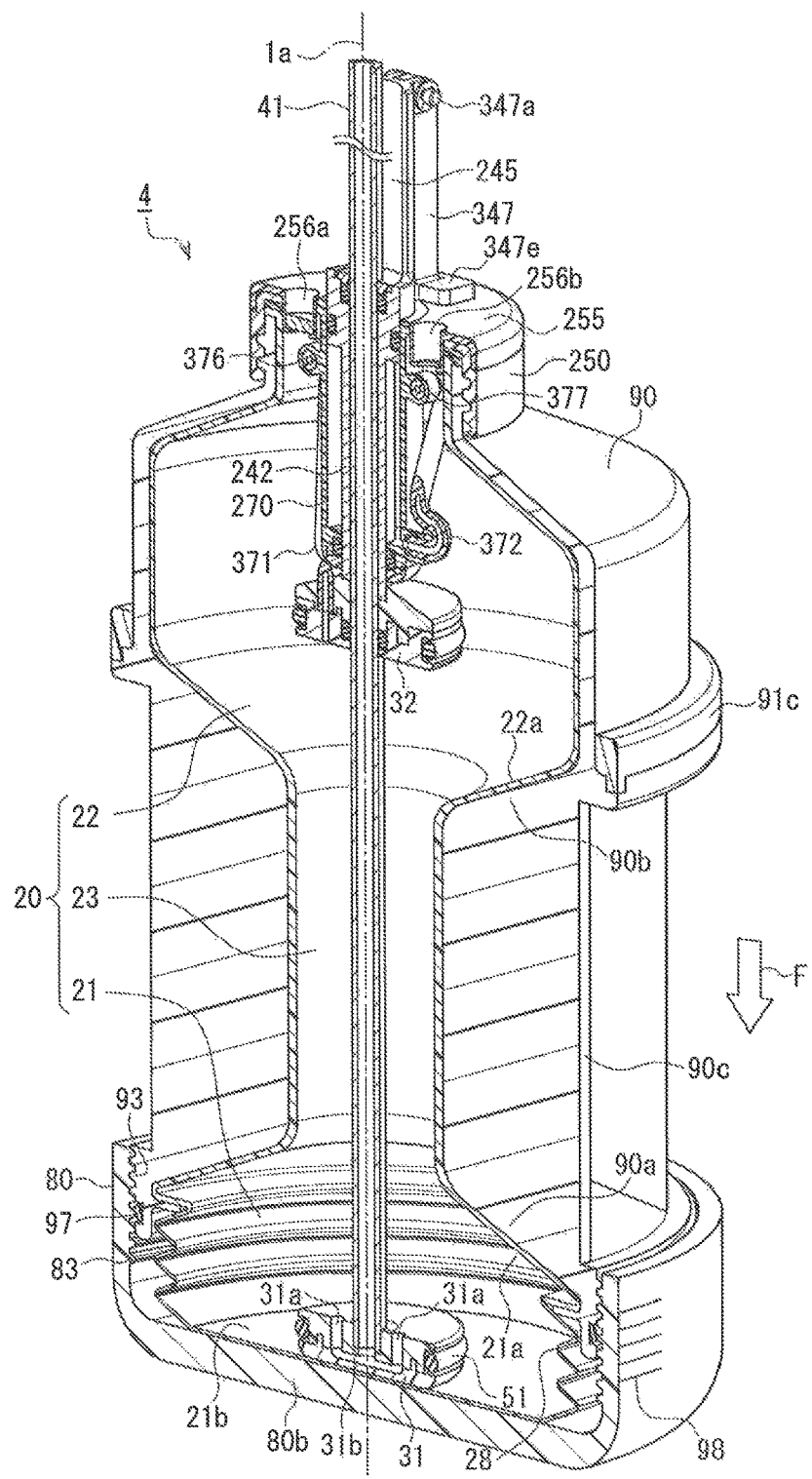
FIG. 19 is a cross-sectional perspective view of a blood component separation device of Embodiment 4 of the present invention.

FIG. 18 is a perspective view of the device 4. FIG. 19 is a cross-sectional perspective view taken along the longitudinal direction of the device 4. In FIG. 19, an alternate long and short dash line la is a central axis of the device 4.

As illustrated in FIG. 19, the first blocking member 31 is held at the lower end of the first hollow cylindrical rod 41. The first rod 41 extends upward along the central axis 1a and reaches the outside of the blood reservoir 20. The first rod 41 in Embodiment 3 does not have the first hole 41a and a plurality of second holes 41b, which are formed in the first rod 41 in Embodiments 2, 3 (see FIGS. 6 and 14). Moreover, the first rod 41 in Embodiment 4 does not contain the tube 43, which is inserted into the first rod 41 in Embodiments 2, 3 (see FIGS. 6 and 14).

The upper surface of the first blocking member 31 has two openings 31a. The two openings 31a communicate with each other via a substantially "U"-shaped flow path 31b formed in the first blocking member 31. The lower end of the first rod 41 is inserted into the first blocking member 31 and connected to a substantially central portion of the flow path 31b. Therefore, the first rod 41 communicates with the openings 31a in the first blocking member 31.

Figure 20:
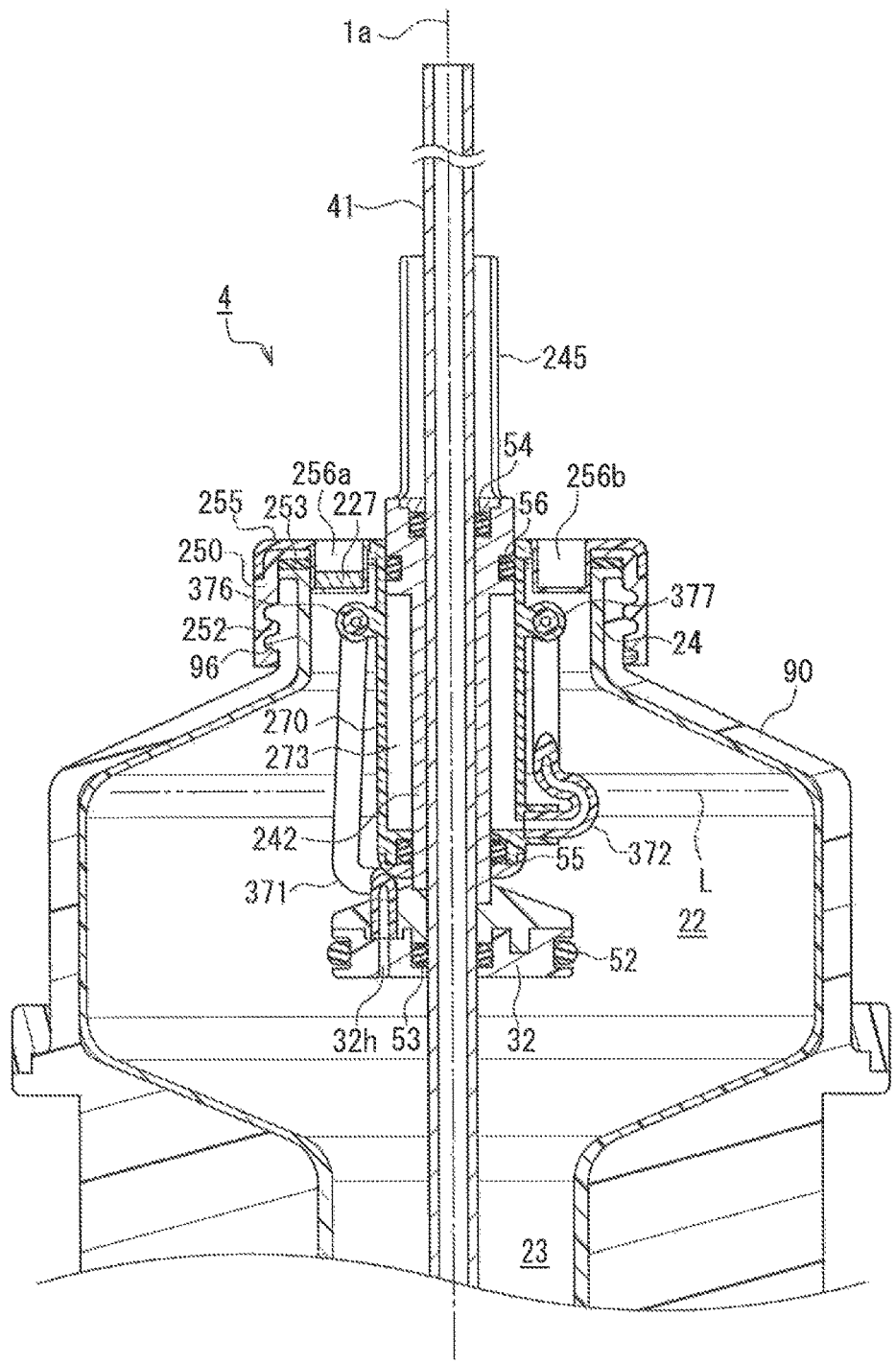
FIG. 20 is an enlarged cross-sectional view of a second blocking member and its periphery in a blood component separation device of Embodiment 4 of the present invention.

FIG. 20 is an enlarged cross-sectional view of the second blocking member 32 and its periphery. The second blocking member 32 is held at the lower end of the second rod 242.

The second blocking member 32 has the through hole 32h, which penetrates the second blocking member 32 in the vertical direction. This configuration is the same as that in Embodiment 3. However, the through hole 32h does not have the one-way valve 235, which is provided in the through hole 32h in Embodiment 3 (see FIG. 15). In this embodiment, the lower end of a first flexible hollow tube 371 is inserted into the through hole 32h from above. The upper end of the first tube 371 is inserted into and held by a first holder 376 provided in the vicinity of the upper end of the guide cylinder 270.

Instead of the air pipe 272 in Embodiment 3 (see FIG. 15), the lower end of a second flexible hollow tube 372 is connected to the guide cylinder 270 in Embodiment 4. The hermetically sealed space 273 between the second rod 242 and the guide cylinder 270 communicates with the second tube 372. The upper end of the second tube 372 is inserted into and held by a second holder 377 provided in the vicinity of the upper end of the guide cylinder 270.

In FIG. 20, an alternate long and two short dashes line L indicates the typical position of a blood surface during the use of the device 4. The upper ends of the first tube 371 and the second tube 372 are positioned higher than the blood surface L and are open in the horizontal direction in the blood reservoir 20.

The top 255 has two ports 256a, 256b. The ports 256a, 256b are through holes that connect the inside of the blood reservoir 20 to the outside. The port 256a is provided with the vent filter 227 having the same function as that of the vent filter 27 in Embodiment 1. The port 256b is a blood injection port for injecting blood into the blood reservoir 20. The blood injection port 256b may be connected to, e.g., one end of a soft tube. In this case, the other end of the soft tube may be provided with a known female connector.

The second rod 242 has the operating piece 245 that extends upward from the portion having the hollow cylindrical shape. The operating piece 245 protrudes above the top 255. As illustrated in FIGS. 18 and 19, a stopper 347 is connected to the upper end of the operating piece 245 via a rotation axis 347a along the horizontal direction. The stopper 347 can be rotated around the rotation axis 347a. In FIGS. 18 and 19, the stopper 347 is located outside the operating piece 245 (i.e., the side of the operating piece 245 facing away from the central axis 1a) so as to overlap the operating piece 245. When the stopper 347 is at this position, a stopper end 347e, i.e., the tip of the stopper 347 (the opposite end of the stopper 347 to the rotation axis 347a) is in contact with the upper end of the guide cylinder 270 or the upper surface of the top 255. Therefore, when the stopper 347 is at this position, the second rod 242 cannot be moved down. In the present invention, this state is called a "locked state" by the stopper 347. Embodiment 3 does not use the removable stopper 247 as described in Embodiment 2.

In FIG. 19, the lower surface of the first blocking member 31 is in contact with the bottom surface of the first storage section 21. The second blocking member 32 is hanging in the second storage section 22 and does not come into contact with the inner circumferential surface of the second storage section 22. The positions of the first blocking member 31 and the second blocking member 32 as illustrated in FIG. 19 are called "initial positions".

The configuration of the support halves 91a, 91b is substantially the same as that in Embodiment 2. In this embodiment, however, an annular support ring 91c is attached to the outer circumferential surface of the support halves 91a, 91b to prevent the two support halves 91a, 91b attached to the blood reservoir 20 from being separated (see FIGS. 18 and 19). The use of the support ring 91c is advantageous to improve the workability of assembly of the support halves 91a, 91b and the blood reservoir 20.

[Method of Use]

Using the device 4 having the above configuration, a method for separating collected blood into different blood components by centrifugation will be described.

Blood (bone marrow fluid) that is to be centrifuged is collected in the same manner as Embodiments 1 to 3. A blood volume and a hematocrit value of the blood are measured, and then a red blood cell volume and a plasma volume are calculated.

The empty device 4 is prepared, in which the first blocking member 31 and the second blocking member 32 are at the initial positions as illustrated in FIG. 19. The bottom cap 80 is rotated to adjust the amount of contraction deformation of the bellows structure 28 so that the buffy coat will be formed within the third storage section 23 of the blood reservoir 20 after centrifugation. Similarly to Embodiments 1 to 3, the amount of contraction deformation may be adjusted by using the marks 98.

Next, the collected blood is injected into the blood reservoir 20 via the blood injection port 256b formed in the top 255. Then, the blood injection port 256b is liquid-tightly sealed. As illustrated in FIG. 20, the blood surface L is positioned lower than the openings of the upper ends of the first tube 371 and the second tube 372.

Subsequently, the device 4 filled with blood is mounted in a centrifuge, followed by centrifugation. The centrifugal force acts parallel to the central axis 1a in the direction of the arrow F in FIGS. 18 and 19. The lower surface of the first blocking member 31 is in contact with the bottom surface of the first storage section 21. The stopper 347 coupled to the second rod 242 is in the locked state. Therefore, the vertical positions of the first blocking member 31 and the second blocking member 32 remain unchanged from their initial positions, even if the centrifugal force F acts on them during centrifugation.

After centrifugation, the device 4 is taken out of the centrifuge. The formation of the buffy coat in the third storage section 23 is confirmed. The fine adjustment of the vertical position of the buffy coat may be made as needed by rotating the bottom cap 80.

Figure 21:
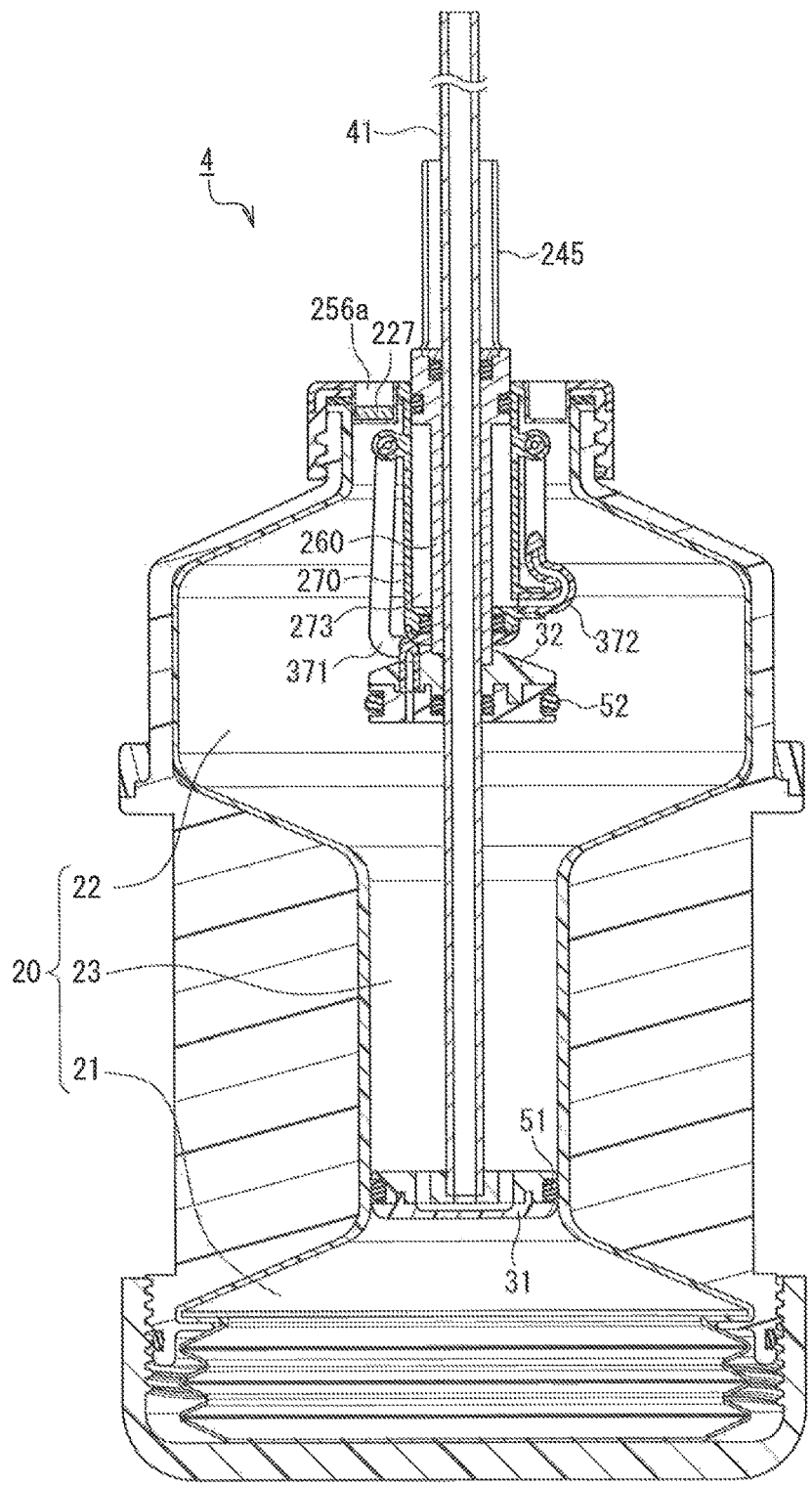
FIG. 21 is a cross-sectional view of a blood component separation device of Embodiment 4 of the present invention, in which the communication between a first storage section and a third storage section is blocked by a first blocking member.

Next, the first rod 41 is pulled up by holding the upper end of the first rod 41. Then, as illustrated in FIG. 21, the first blocking member 31 is fitted into the lower opening of the third storage section 23. Thus, the first blocking member 31 closes the opening of the third storage section 23 on the first storage section 21 side. Consequently, the communication between the first storage section 21 and the third storage section 23 is liquid-tightly blocked by the first blocking member 31. The second blocking member 32 still remains in the initial position (see FIG. 19).

Next, the stopper 347 is rotated from the position as illustrated in FIGS. 18 and 19, thereby releasing the locked state. Subsequently, the operating piece 245 is pressed down. As the second rod 242 moves downward, the volume of the hermetically sealed space 273 is reduced. Accordingly, air that is already present in the hermetically sealed space 273 flows into the second storage section 22 through the second tube 372, and then is discharged from the device 4 to the outside through the vent filter 227 in the port 256a. Therefore, the pressure in the hermetically sealed space 273 is not increased, which facilitates the operation of moving the second rod 242 down.

Figure 22:
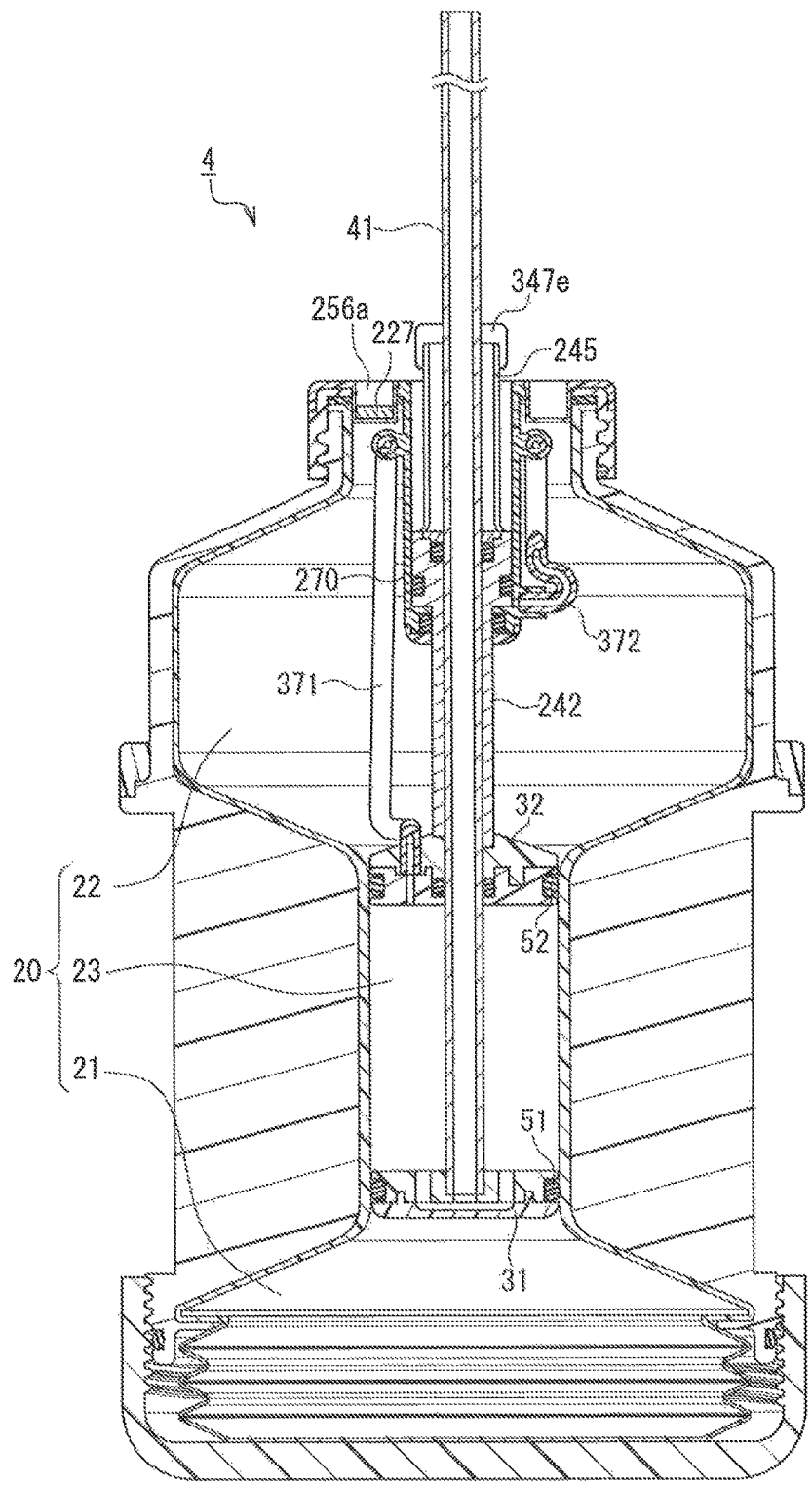
FIG. 22 is a cross-sectional view of a blood component separation device of Embodiment 4 of the present invention, in which the communication between a first storage section and a third storage section is blocked by a first blocking member, and the communication between a second storage section and the third storage section is blocked by a second blocking member.

As illustrated in FIG. 22, the operating piece 245 is operated to fit the second blocking member 32 into the upper opening of the third storage section 23. Thus, the second blocking member 32 closes the opening of the third storage section 23 on the second storage section 22 side. Consequently, the communication between the second storage section 22 and the third storage section 23 is liquid-tightly blocked by the second blocking member 32. The first blocking member 31 has not been displaced from the position as illustrated in FIG. 21. The first tube 371 is deformed due to the downward movement of the second blocking member 32.

In this manner, the first storage section 21 in which the red blood cell components have been stored, the third storage section 23 in which the white blood cell components have been stored, and the second storage section 22 in which the plasma components have been stored are liquid-tightly separated from one another.

Figure 23:
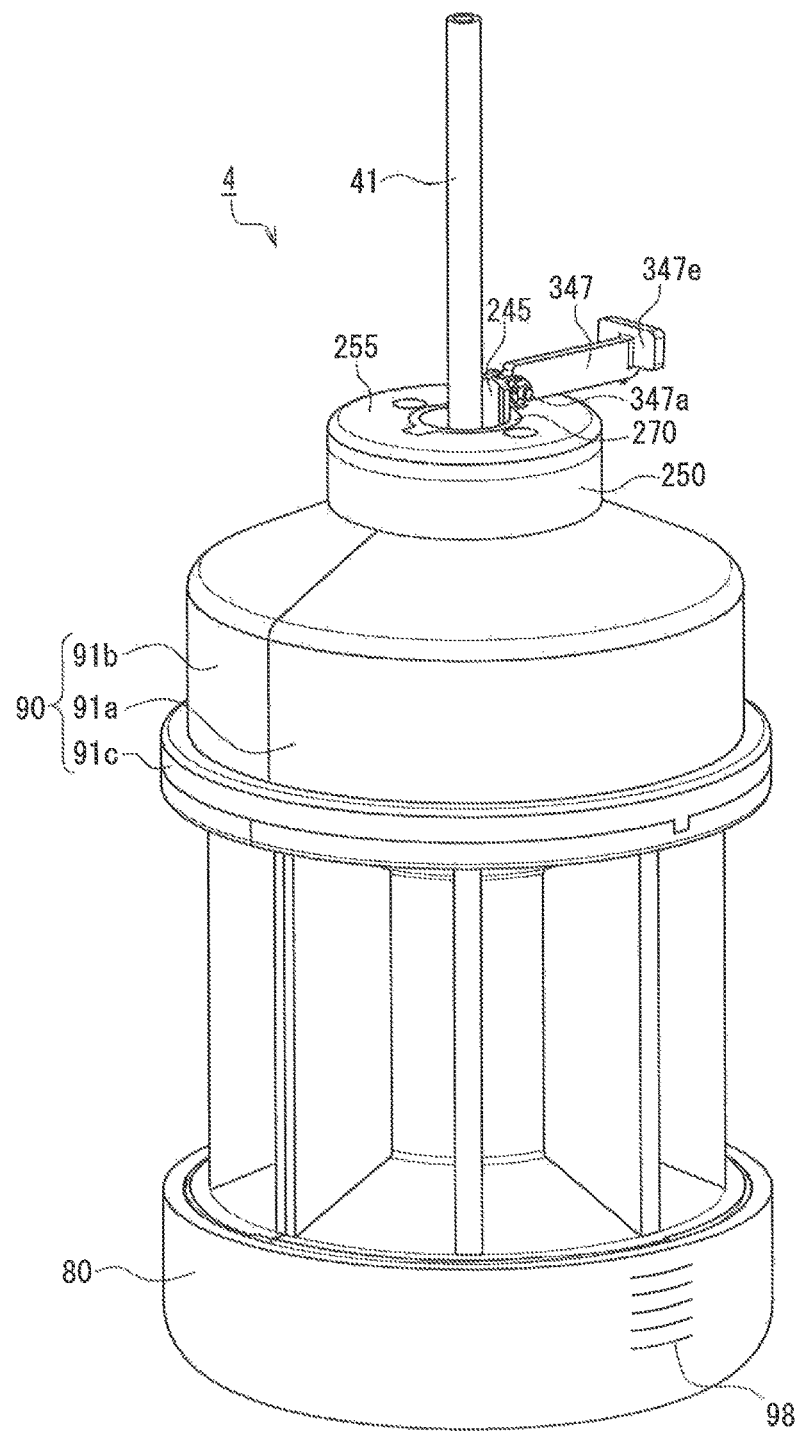
FIG. 23 is a perspective view of a blood component separation device of Embodiment 4 of the present invention, in which the device is in the state as illustrated in FIG. 22.

FIG. 23 is a perspective view of the device 4 in which the second blocking member 32 closes the upper opening of the third storage section 23 as illustrated in FIG. 22. The stopper 347 is rotated around the rotation axis 347a and protrudes above the top 255. Most of the operating piece 245 is housed in the guide cylinder 270. In Embodiment 4, since the stopper 347 is rotatably coupled to the end of the operating piece 245, even if the length of the operating piece 245 is reduced, the operation of closing the upper opening of the third storage section 23 with the second blocking member 32 can be easily performed by operating the stopper 347. Unlike the stopper 47 in Embodiment 2 (see FIG. 8) and the stopper 247 in Embodiment 3 (see FIG. 13), the stopper 347 is coupled to the operating piece 245 of the second rod 242. Thus, there is no possibility of losing the stopper 347.

Next, the mouth (male luer) of an empty syringe is connected to the upper end of the first rod 41 via a soft tube or the like, and a plunger of the syringe is pulled. Thus, the white blood cell components in the third storage section 23 are aspirated and collected into the syringe via a flow path (first flow path 261) that connects the openings 31a in the upper surface of the first blocking member 31, the flow path 31b, and the first rod 41, as indicated by the arrows 65 in FIG. 24. As the white blood cell components move from the third storage section 23 to the syringe, outside air enters the third storage section 23 through a flow path (second flow path 262) that connects the vent filter 227 in the port 256a (see FIG. 22), the first tube 371, and the through hole 32h of the second blocking member 32, as indicated by the arrow 66 in FIG. 24. Therefore, the pressure in the third storage section 23 does not become excessively negative, and the white blood cell components can be easily collected.

Moreover, similarly to Embodiments 2, 3, a physiological saline may be injected into the third storage section 23 via the first flow path 261 in the first rod 41. Then, the physiological saline is collected via the first flow path 261 in the first rod 41. As the physiological saline flows in/out of the third storage section 23 via the first flow path 261, air flows out of/in the third storage section 23 via the second flow path 262. Thus, the remaining white blood cell components in the third storage section 23, the first rod 41, and the flow path 31b can be collected with the physiological saline.

[Effects]

Embodiment 4 has the following effects in addition to the effects of Embodiment 3.

In Embodiment 4, the first rod 41 does not contain the tube 43, which is present in the first rod 41 in Embodiments 2, 3. This eliminates the operation of inserting the tube 43 into the first rod 41, and therefore is advantageous to simplify the assembly operation of the device 4. Moreover, the cross section of the flow path (i.e., the first flow path 261) in the first rod 41 is enlarged when the white blood cell components in the third storage section 23 are aspirated and collected via the first rod 41. This reduces the flow resistance, and therefore is advantageous to facilitate the operation of collecting the white blood cell components.

The white blood cell components in the third storage section 23 flow from the openings 31a in the upper surface of the first blocking member 31 to the first rod 41 through the flow path 31b. Therefore, the first rod 41 does not need to have a hole in the outer circumferential surface, through which the white blood cell components flow in. Moreover, the air that is to enter the third storage section 23 in place of the white blood cell components passes through the first tube 371 and the through hole 32h of the second blocking member 32 in sequence, rather than through the first rod 41, and into the third storage section 23. Therefore, the first rod 41 does not need to have a plurality of second holes 41b as in the case of Embodiments 2, 3. Consequently, the structure of the first rod 41 in this embodiment is simple because no hole is formed in the outer circumferential surface of the first rod 41. In addition, since the mechanical strength of the first rod 41 is improved, the operation of closing the lower opening of the third storage section 23 with the first blocking member 31 can be easily and reliably performed by operating the first rod 41.

However, a through hole may be formed in the outer circumferential surface of the first rod 41 at the position near the first blocking member 31, and the white blood cell components may be collected via the through hole. In this case, the openings 31a and the flow path 31b of the first blocking member 31 are not necessary.

The through hole 32h of the second blocking member 32 and the first hollow tube 371 connected to the through hole 32h constitute the pressure release mechanism. When the pressure in the third storage section 23 becomes positive with the movement of the second blocking member 32 to close the upper opening of the third storage section 23, the white blood cell components in the third storage section 23 flow through the through hole 32h and the first tube 371 and into the second storage section 22. This can prevent an abnormal increase in the pressure in the third storage section 23.

The pressure release mechanism of Embodiment 3 includes the through hole 32h of the second blocking member 32 and the one-way valve 235 provided in the through hole 32h. In this configuration, the one-way valve 235 does not open depending on the extent of the positive pressure in the third storage section 23, and therefore, in some cases, the pressure in the third storage section 23 may not be released. On the other hand, the pressure release mechanism in this embodiment is configured only by connecting the first hollow tube 371 to the through hole 32h of the second blocking member 32. The pressure release mechanism has no valve and thus can reliably release the pressure in the third storage section 23 regardless of the extent of the positive pressure in the third storage section 23. This configuration improves the reliability of the operation of the pressure release mechanism, and also can prevent leakage of the white blood cell components to the outside and the malfunction, as described in Embodiment 3. This is advantageous to improve the rate of collection of white blood cell components.

The upper end of the first tube 371 is open above the blood surface L in the blood reservoir 20. Therefore, when the white blood cell components in the third storage section 23 are aspirated and collected after the first blocking member 31 and the second blocking member 32 close the lower opening and the upper opening of the third storage section 23, respectively (see FIG. 24), the plasma components in the second storage section 22 will not flow into the third storage section 23 through the first tube 371. Moreover, since the port 256a is provided with the vent filter 227, the white blood cell components flowing from the third storage section 23 through the first tube 371 will not leak out of the device 4.

The first holder 376 holds the first tube 371 so that the opening of the upper end of the first tube 371 is oriented in the horizontal direction. Therefore, the vent filter 227 is not likely to be wet with the white blood cell components that have flowed through the first tube 371. Even if the first tube 371 is pulled downward as the second blocking member 32 moves downward, the first tube 371 is not likely to fall off the holder 376.

Figure 24:
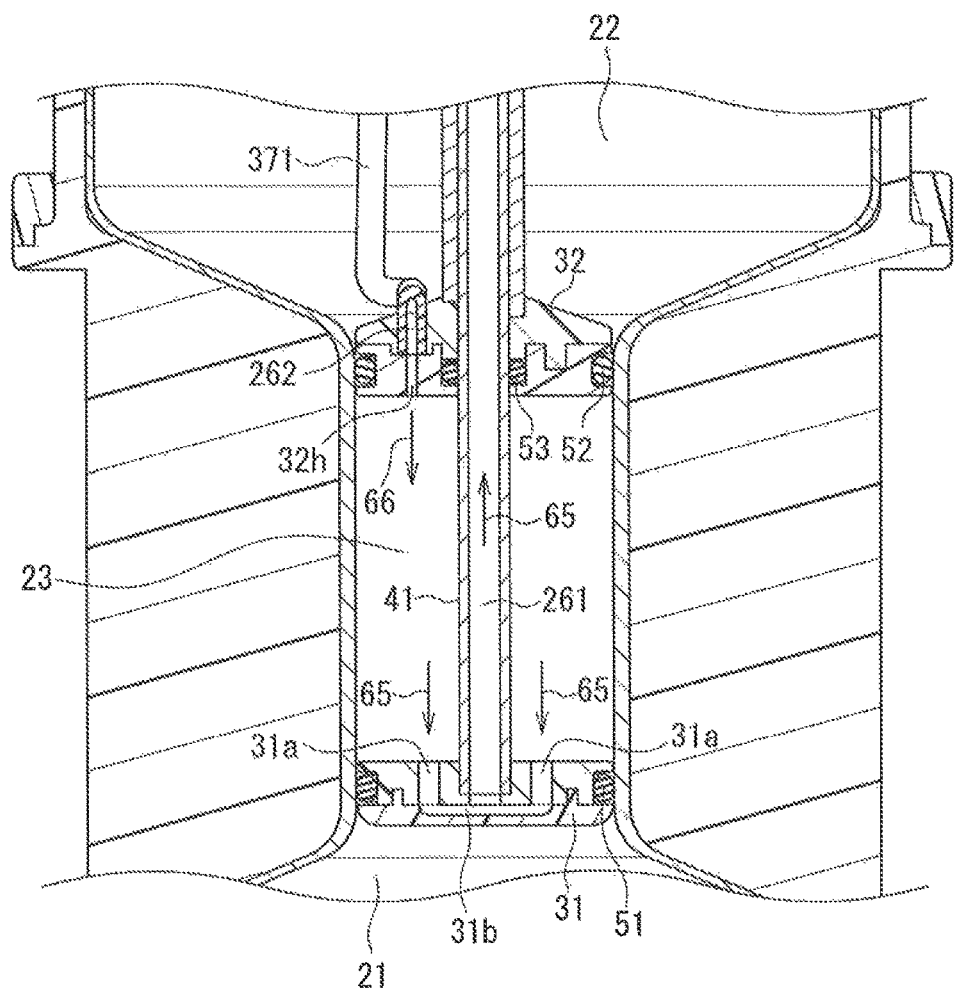
FIG. 24 is an enlarged cross-sectional view illustrating the flow of a fluid when white blood cell components in a third storage section are collected in a blood component separation device of Embodiment 4 of the present invention.
Figure 25:
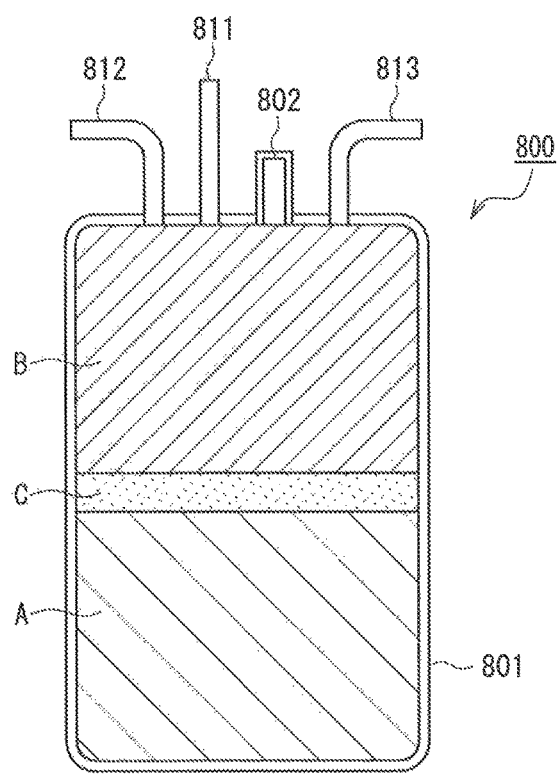
FIG. 25 is a schematic vertical cross-sectional view illustrating a conventional blood bag used for separation of blood into blood components.
Figure 26:
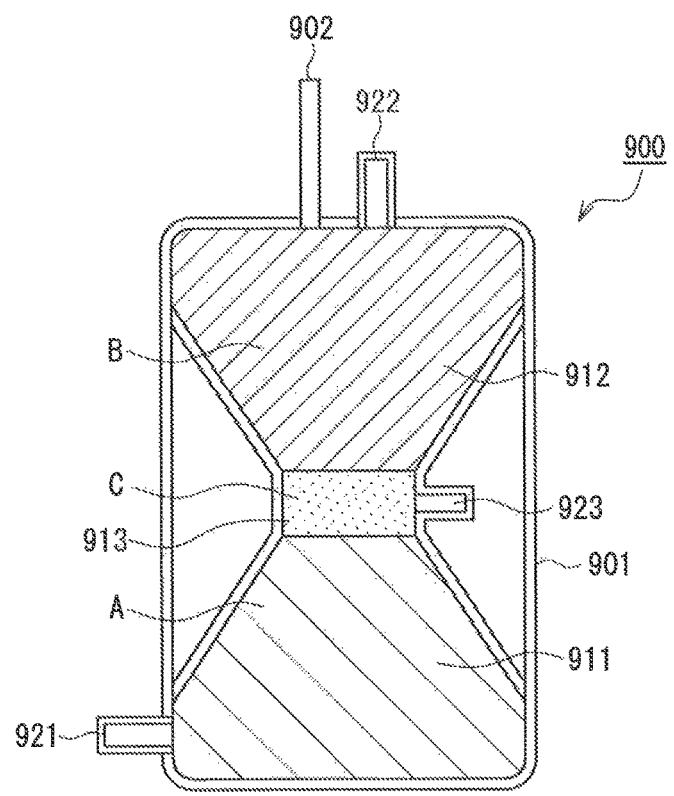
FIG. 26 is a schematic vertical cross-sectional view illustrating an improved conventional blood bag used for separation of blood into blood components.

As illustrated in FIG. 24, the pressure release mechanism of this embodiment also functions as the second flow path 262 for introducing outside air into the third storage section 23 in place of the white blood cell components when the white blood cell components in the third storage section 23 are collected via the first flow path 261. In Embodiment 3, the pressure release mechanism cannot function as the second flow path, and therefore the second flow path needs to be provided in addition to the pressure release mechanism. In this embodiment, since the pressure release mechanism and the second flow path can share their members, the number of parts of the device 4 can be reduced, and thus the configuration of the device 4 can be simplified.

Except for the above, Embodiment 4 is the same as Embodiments 1 to 3. The description of Embodiments 1 to 3 can also be applied to Embodiment 4.

(Various Modified Examples)

Embodiments 1 to 4 are merely illustrative. The present invention is not limited to Embodiments 1 to 4 and may be appropriately modified.

In Embodiments 1 to 4, the bellows adjustment mechanism is configured to adjust the amount of contraction by allowing the bellows structure 28 to contact in the vertical direction. However, the bellows adjustment mechanism may be configured to adjust the amount of expansion by allowing the bellows structure 28 to expand in the vertical direction.

In Embodiments 1 to 4, the support member 90 and the bottom cap 80 have the male thread 93 and the female thread 83, respectively, which constitute the bellows adjustment mechanism for adjusting the amount of expansion or contraction of the bellows structure 28. However, the support member 90 may have a female thread and the bottom cap 80 may have a male thread.

In Embodiments 1 to 4, the bellows adjustment mechanism is configured to adjust the amount of contraction of the bellows structure 28 with the rotational position of the bottom cap 80 relative to the support member 90 or the depth of screwing of the male thread 93 into the female thread 83. However, the amount of contraction of the bellows structure 28 may be adjusted by any method other than the above. For example, the support member 90 may be fitted into/onto the bottom cap 80 with a plate-like member being interposed between the bottom 80b of the bottom cap 80 and the bottom 21b of the first storage section 21. The plate-like member has a thickness that corresponds to the amount of contraction of the bellows. In this case, the plate-like member is used to raise the level of the bottom 80b of the bottom cap 80. Therefore, the bellows structure 28 is able to contract in a desired amount at the time the support member 90 is fitted into/onto the bottom cap 80 even without any adjustment of the depth of screwing.

The third storage section 23 may have a second bellows structure and a second bellows adjustment mechanism that are the same as the bellows structure 28 and the bellows adjustment mechanism in Embodiments 1 to 4. The thickness (i.e., the size in the vertical direction) of the buffy coat after centrifugation may vary depending on blood. When the third storage section 23 has the second bellows structure and the second bellows adjustment mechanism, the dimension of the third storage section 23 in the vertical direction can be changed in accordance with the thickness of the buffy coat. Therefore, this configuration can further improve the rate of collection of white blood cell components.

The members other than the support member 90 may have the male thread 93, and the members other than the bottom cap 80 may have the female thread 83. For example, the blood reservoir 20 may have at least one of the male thread 93 and the female thread 83 that constitute the bellows adjustment mechanism. For example, the male thread 93 may be provided in the position above the bellows structure 28 of the blood reservoir 20. In this case, the support member 90 may be omitted if the blood reservoir 20 has a strength high enough to prevent deformation caused by the centrifugal force during centrifugation. Alternatively, the male thread 93 may be provided in the position under the bellows structure 28 of the blood reservoir 20. In this case, the skirt portion 92 of the support member 90 is extended downward, and a female thread is formed on the inner circumferential surface of the skirt portion 92. The bottom cap 80 may be omitted. The amount of expansion of the bellows structure 28 can be adjusted by rotating the support member 90 relative to the blood reservoir 20.

The configuration of the support member 90 is not limited to Embodiments 1 to 4. In Embodiments 1 to 4, the support member 90 is composed of the two support halves 91a, 91b. However, the support member may be composed of three or more members. Moreover, the support member may be composed of a plurality of columnar members that are spaced apart from each other in the circumferential direction (i.e., the direction of rotation about the central axis 1a). The support member 90 may be omitted if the blood reservoir 20 has a strength high enough to prevent deformation caused by the centrifugal force during centrifugation, e.g., by forming the support member integrally with the part(s) constituting the blood reservoir 20.

The structure for blocking the communication between the first storage section and the third storage section and the communication between the second storage section and the third storage section after centrifugation is not limited to Embodiments 1 to 4. For example, two balloons may be placed in the boundary portions between the third storage section and each of the first storage section and the second storage section, respectively. A fluid is injected into the balloons so that the balloons are inflated to be able to block the communications between the third storage section and each of the first storage section and the second storage section. Alternatively, two sets of blades, each of which can be opened and closed and has the same structure as a lens shutter, may be placed in the boundary portions between the third storage section and each of the first storage section and the second storage section, respectively. The sets of blades are operated from the outside of the blood reservoir to be able to block the communications between the third storage section and each of the first storage section and the second storage section. Alternatively, the boundary portions between the third storage section and each of the first storage section and the second storage section may be formed of tubes with flexibility. The tubes are clamped and closed to be able to block the communications between the third storage section and each of the first storage section and the second storage section.

In Embodiments 2 to 4, in order to form a liquid-tight seal, the first O ring 51 is attached to the first blocking member 31, and the second O ring 52 and the third O ring 53 are attached to the second blocking member 32. However, when the first blocking member 31 and the second blocking member 32 themselves are made of materials having rubber elasticity (also referred to as elastomers), the O rings 51, 52, 53 may be omitted. In this case, the materials having rubber elasticity that can be used for the first blocking member 31 and the second blocking member 32 are not particularly limited, and may be, e.g., rubber such as natural rubber, isoprene rubber, and silicone rubber, or thermoplastic elastomers such as styrene elastomer, olefin elastomer, and polyurethane elastomer. The use of the materials having rubber elasticity for the first blocking member 31 and the second blocking member 32 may improve the assembly operation of the device, e.g., in which the first blocking member 31 fixed to the end of the first rod 41 is inserted through the third storage section 23 from the second storage section 22 and is placed in the first storage section 21.

In Embodiments 2, 3, both the first flow path 61 and the second flow path 62 are formed in the first rod 41. However, the present invention is not limited thereto. For example, in Embodiment 2, the second rod 42 may be formed of a hollow rod-like member. Then, the lower end of the second rod 42 may be inserted into the through hole that penetrates the second blocking member 32 in the vertical direction, and the upper end of the second rod 42 may pass through the operating piece 45 and open upward. Thus, a second flow path, which provides a communication between the liquid-tightly sealed third storage section 23 and the outside of the blood reservoir 20, can be formed in the second rod 42. In this case, only one flow path (first flow path) is required in the first rod 41. Therefore, the tube 43 is not necessary. Moreover, the first rod 41 does not need to have the second holes 41b.

Alternatively, a plurality of ports that communicate with the third storage section 23 may be provided in the outer wall of the third storage section 23. When a physiological saline is injected into the third storage section 23 from some of the ports, the white blood cell components can be collected with the physiological saline from the remaining ports. In this case, there is no need to form the first flow paths 61, 261 (and the second flow path 62) in the first rod 41, and the first rod 41 may be a solid rod-like member.

INDUSTRIAL APPLICABILITY

The field of application of the present invention is not particularly limited, and the present invention can be widely used in the field that requires centrifugation of blood. Among others, the present invention can be preferably used in the fields of (i) separation of blood into blood components, e.g., for blood component transfusion in which only necessary components in blood are transfused into a patient; (ii) bone marrow transplantation in which white blood cell components are mainly used; and (iii) regenerative medicine.

DESCRIPTION OF REFERENCE NUMERALS

1, 2, 3, 4 Blood component separation device
20 Blood reservoir
21 First storage section
22 Second storage section
23 Third storage section
28 Bellows structure
31 First blocking member
32 Second blocking member
32h Through hole (pressure release mechanism)
41 First rod (outer tube)
42 Second rod
43 Tube (inner tube)
47, 247, 347 Stopper (movement restriction mechanism)
61, 261 First flow path
62 Second flow path
80 Bottom cap
83 Female thread (bellows adjustment mechanism)
90 Support member
93 Male thread (bellows adjustment mechanism)
98 Mark
235 One-way valve (pressure release mechanism)
242 Second rod
245 Operating piece of second rod
371 First tube (pressure release mechanism)

The invention claimed is:

1. A blood component separation device, comprising:
a blood reservoir configured to store blood and used for centrifugation of blood stored in the blood reservoir, wherein the blood reservoir comprises:
a first storage section, a second storage section, and a third storage section that is provided between the first storage section and the second storage section, and communicates with the first storage section and the second storage section,
a support member configured to prevent deformation of the third storage section during centrifugation;
a bottom cap that is in contact with at least a part of a bottom of the first storage section, wherein one of the support member and the bottom cap has a male thread and the other of the support member and the bottom cap has a female thread;
a bellows structure provided on the blood reservoir, configured to be expandable and contractable; and
a bellows adjustment mechanism comprising the male thread and the female thread, and configured to adjust an amount of expansion or contraction of the bellows structure based on a depth of screwing the male thread into the female thread, which adjusts the amount of expansion or contraction of the bellows structure,
wherein a volume of the blood reservoir is adjusted by adjusting the bellows structure using the bellows adjustment mechanism.

2. The blood component separation device according to claim 1, wherein the bellows structure is provided on the first storage section that stores red blood cell components after centrifugation.

3. The blood component separation device according to claim 1, wherein the blood reservoir is integrally formed as a single piece, including the bellows structure.

4. The blood component separation device according to claim 1, wherein the bottom cap has a scale that serves as an indicator for adjusting the amount of expansion or contraction of the bellows structure.

5. The blood component separation device according to claim 1, wherein the device is configured so that a communication between the first storage section and the third storage section can be blocked, and a communication between the second storage section and the third storage section can be blocked.

6. The blood component separation device according to claim 1, further comprising a flow path through which blood components in the third storage section flow out of the blood reservoir.

7. The blood component separation device according to claim 1, comprising a first blocking member and a second blocking member in the blood reservoir,
wherein the first blocking member is configured to be able to block the communication between the first storage section and the third storage section, and
the second blocking member is configured to be able to block the communication between the second storage section and the third storage section.

8. The blood component separation device according to claim 7, wherein the first blocking member moves in the first storage section to block the communication between the first storage section and the third storage section.

9. The blood component separation device according to claim 8, comprising a first rod that holds the first blocking member and is drawn out of the blood reservoir,
wherein the first rod is moved to allow the first blocking member to move.

10. The blood component separation device according to claim 9, comprising a first flow path that provides a communication between the third storage section and the outside of the blood reservoir while the first blocking member blocks the communication between the first storage section and the third storage section, and the second blocking member blocks the communication between the second storage section and the third storage section.

11. The blood component separation device according to claim 10, further comprising a second flow path that provides a communication between the third storage section and the outside of the blood reservoir while the first blocking member blocks the communication between the first storage section and the third storage section, and the second blocking member blocks the communication between the second storage section and the third storage section.

12. The blood component separation device according to claim 11, wherein at least one of the first flow path and the second flow path is provided in the first rod.

13. The blood component separation device according to claim 7, wherein the second blocking member moves in the second storage section to block the communication between the second storage section and the third storage section.

14. The blood component separation device according to claim 13, comprising a second rod that holds the second blocking member and is drawn out of the blood reservoir,
wherein the second rod is moved to allow the second blocking member to move.

15. The blood component separation device according to claim 13, further comprising a movement restriction mechanism that restricts a movement of the second blocking member so as to prevent the second blocking member from moving in the blood reservoir and blocking the communication between the second storage section and the third storage section during centrifugation.

16. The blood component separation device according to claim 7, further comprising a pressure release mechanism that releases pressure in the third storage section when the first blocking member blocks the communication between the first storage section and the third storage section, and the second blocking member blocks the communication between the second storage section and the third storage section.

17. The blood component separation device according to claim 16, wherein the pressure release mechanism includes a through hole formed in the second blocking member so as to provide a communication between the second storage section and the third storage section.

18. The blood component separation device according to claim 17, wherein the pressure release mechanism further includes a one-way valve provided in the through hole, and
the one-way valve allows a flow from the third storage section to the second storage section through the through hole, and prevents a flow from the second storage section to the third storage section through the through hole.

19. The blood component separation device according to claim 17, wherein the pressure release mechanism further includes a tube, one end of which is connected to the through hole, and
the other end of the tube is open in a position above a blood surface in the blood reservoir.

20. The blood component separation device according to claim 16, wherein the pressure release mechanism forms a flow path for introducing outside air into the third storage section when white blood cell components in the third storage section are aspirated and collected while the first blocking member blocks the communication between the first storage section and the third storage section, and the second blocking member blocks the communication between the second storage section and the third storage section.

21. A blood component separation device, comprising:
a blood reservoir configured to store blood and used for centrifugation of blood stored in the blood reservoir,
wherein the blood reservoir comprises:
a first storage section, a second storage section, and a third storage section that is provided between the first storage section and the second storage section, and communicates with the first storage section and the second storage section; and
a flow path through which blood components in the third storage section flow out of the blood reservoir;
a bellows structure provided on the blood reservoir, configured to be expandable and contractable; and
a bellows adjustment mechanism comprising a male thread and a female thread, and configured to adjust an amount of expansion or contraction of the bellows structure based on a depth of screwing the male thread into the female thread, which adjusts the amount of expansion or contraction of the bellows structure,
wherein a volume of the blood reservoir is adjusted by adjusting the amount of expansion or contraction of the bellows structure.

22. A blood component separation device, comprising:
a blood reservoir for storing blood and is used for centrifugation of blood stored in the blood reservoir,
wherein the blood reservoir comprises:
a first storage section, a second storage section, and a third storage section that is provided between the first storage section and the second storage section, and communicates with the first storage section and the second storage section, and
a first blocking member and a second blocking member in the blood reservoir,
wherein the first blocking member is configured to block communication between the first storage section and the third storage section,
the second blocking member is configured to block communication between the second storage section and the third storage section;

a bellows structure provided on the blood reservoir, configured to be expandable and contractable; and a bellows adjustment mechanism comprising a male thread and a female thread, and configured to adjust an amount of expansion or contraction of the bellows structure based on a depth of screwing the male thread into the female thread, which adjusts the amount of expansion or contraction of the bellows structure, wherein a volume of the blood reservoir is adjusted by adjusting the amount of expansion or contraction of the bellows structure.

* * * * *